(12) United States Patent
Rothstein et al.

(10) Patent No.: US 9,371,514 B2
(45) Date of Patent: Jun. 21, 2016

(54) HUMAN B1 CELLS AND USES THEREOF

(75) Inventors: Thomas L. Rothstein, Port Washington, NY (US); Daniel O. Griffin, Port Washington, NY (US); Nichol E. Holodick, Roslyn Heights, NY (US)

(73) Assignee: The Feinstein Institute for Medical Research, Manhassett, NY (US)

( * ) Notice: Subject to any disclaimer, the term of this patent is extended or adjusted under 35 U.S.C. 154(b) by 0 days.

(21) Appl. No.: 13/825,375

(22) PCT Filed: Sep. 22, 2011

(86) PCT No.: PCT/US2011/052750
§ 371 (c)(1),
(2), (4) Date: Apr. 30, 2013

(87) PCT Pub. No.: WO2012/040456
PCT Pub. Date: Mar. 29, 2012

(65) Prior Publication Data
US 2013/0202624 A1 Aug. 8, 2013

Related U.S. Application Data

(60) Provisional application No. 61/403,845, filed on Sep. 22, 2010.

(51) Int. Cl.
| | |
|---|---|
| *C12N 5/02* | (2006.01) |
| *G01N 33/50* | (2006.01) |
| *C12N 5/0781* | (2010.01) |
| *A61K 35/17* | (2015.01) |
| *G01N 33/564* | (2006.01) |
| *G01N 33/569* | (2006.01) |
| *G01N 33/574* | (2006.01) |
| *A61K 39/395* | (2006.01) |
| *G01N 33/68* | (2006.01) |
| *A61K 35/12* | (2015.01) |

(52) U.S. Cl.
CPC .............. *C12N 5/0635* (2013.01); *A61K 35/17* (2013.01); *A61K 39/3955* (2013.01); *G01N 33/564* (2013.01); *G01N 33/56972* (2013.01); *G01N 33/57426* (2013.01); *G01N 33/6893* (2013.01); *A61K 2035/124* (2013.01); *G01N 2333/70507* (2013.01); *G01N 2333/70553* (2013.01)

(58) Field of Classification Search
None
See application file for complete search history.

(56) References Cited

U.S. PATENT DOCUMENTS

2005/0276803 A1   12/2005   Chen et al.

FOREIGN PATENT DOCUMENTS

WO   2005027841 A2   3/2005

OTHER PUBLICATIONS

Caligaris-Cappio F et al., entitled "Infrequent Normal B Lymphocytes Express Features of B Chronic Lymphocytic Leukemia,"J. Exp. Med., 1982, vol. 155, No. 2, pp. 623-628.
Klein U et al., entitled "Human immunoglobulin (Ig) M+IgD+ peripheral blood B cells expressing the CD27 cell surface antigen carry somatically mutated variable region genes: CD27 as a general marker for somatically mutated (Memory) B cells," J. Exp. Med., Nov. 2, 1998, vol. 188, No. 9, pp. 1679-1689.
Dauphinee M et al., entitled "B Cells Expressing CD5 Are Increased in Sjogren's Syndrome," 1988, vol. 31, No. 5, pp. 642-647.
Holodick N E et al., entitled "Adult BM generates CD5+ B1 cells containing abundant N-region additions," Eur. J. Immunol, Aug. 27, 2009, vol. 39, No. 9, pp. 2383-2394.
Holodick N E et al., entitled "Continual signaling is responsible for constitutive ERK phosphorylation in B-1 a cells," Molecular Immunology, Sep. 1, 2009, vol. 46, No. 15, pp. 3029-3036.
Agematsu K et al., entitled "CD27/CD70 interaction directly drives B cell IgG and IgM synthesis," Eur. J. Immunol, 1995, vol. 25, No. 10, pp. 2825-2829.
Alter-Wolf et al., entitled "Old mice bone marrow B1 progenitors, but lose B2 precursors, and exhibit altered immature B cell phenotype and light chain usage," Mech Ageing Dev, Jun. 2009, vol. 130, No. 6, pp. 401-408.
Dono et al., entitled "CD5+ B cells with features of subepithelial B cells found in human tonsils," Eur J Immunol 2007, vol. 37, pp. 2138-2147.
Racine et al., entitled "CD11c expression identifies a population of extrafollicular antigen-specific splenic plasmablasts responsible for CD4 T-independent antibody response during intracellular bacterial infection," J Immunol, 2008, vol. 181, pp. 1375-1385.

*Primary Examiner* — Ronald Schwadron
(74) *Attorney, Agent, or Firm* — Amster, Rothstein & Ebenstein LLP

(57) ABSTRACT

The present invention is directed to isolated populations of human natural immunoglobulin-producing B1 lymphocytes, wherein the B1 lymphocytes display surface biomarkers CD20, CD43 and CD27 and are either CD11b+ or GD11b−. The present invention is also directed to a method of isolating human natural immunoglobulin-producing B1 lymphocytes from a blood sample comprising isolating B lymphocytes from the sample that express surface biomarkers CD20, CD43 and CD27, and, optionally, CD11b. In addition, the present invention is directed to a methods for diagnosing a B1 cell disorder in a patient, determining the prognosis of a patient having a B1 cell disorder, and treating a patient having a B1 cell disorder.

6 Claims, 17 Drawing Sheets

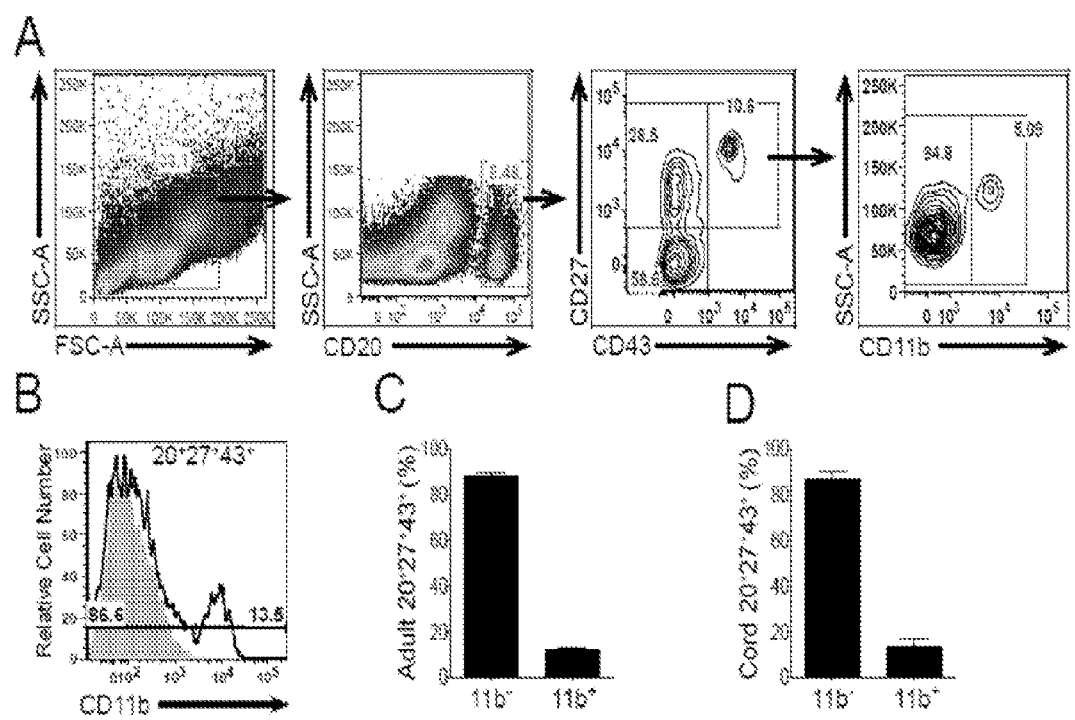
Fig 9A-D

HUMAN B1 CELLS AND USES THEREOF

CROSS-REFERENCE TO RELATED APPLICATIONS

This application is a U.S. national stage entry under 35 U.S.C. X371 of PCT International Patent Application No. PCT/US2011/052750, filed Sep. 22, 2011, and claims priority to U.S. Provisional Patent Application No. 61/403,845, filed Sep. 22, 2010, the contents of which are incorporated herein by reference in their entirety.

STATEMENT OF GOVERNMENT SUPPORT

This invention was made with government support under grant A1029690 awarded by the National institutes of Health. The government has certain rights in the invention.

FIELD OF THE INVENTION

The present invention relates to the identification of the phenotype of human B1 cells and subpopulations, and the uses of the same in diagnostic, prognostic and therapeutic applications in disorders relating to B1 cells including autoimmune diseases such as systemic lupus erythematosus and certain cancers involving B lymphocytes such as chronic lymphocytic leukemia.

BACKGROUND OF THE INVENTION

B lineage expression of the 67 kDa pan-T cell antigen, CD5, was first detected on the surface of certain human and murine malignancies 30 years ago and was subsequently identified on a subset of normal B cells in both species (reviewed in (Hardy and Hayakawa, 2001; Kantor and Herzenberg, 1993; Morris and Rothstein, 1994)). In mice, CD5 expression identifies a distinct B cell lineage, termed B1, that manifests unique ontologic, anatomic, and functional characteristics. In contrast to conventional B2 cells, murine B1 cells derive from CD19+ B220− progenitors, appear early in development, and preferentially locate to coelomic cavities (reviewed in (Berland and Wortis, 2002; Dorshkind and Montecino-Rodriguez, 2007; Herzenberg, 2000; Rothstein, 2002)). Most importantly, B1 cells differ functionally from B2 cells by spontaneously secreting "natural" immunoglobulin that is generated in the absence of specific immunization and which accounts for most of the resting IgM, and a large portion of the resting IgA, found in normal serum (Forster and Rajewsky, 1987; Ishida et al., 1992; Kroese et al., 1993; Sidman et al., 1986). This B1 cell-derived natural immunoglobulin differs from B2 cell-derived antibody in being more germline like (as a result of minimal N-region addition and somatic hypermutation), and is broadly reactive and repertoire-selected (Forster et al., 1988; Gu et al., 1990; Hardy et al., 1989; Pennell et al., 1989).

Natural immunoglobulin is vitally important in the early defense against bacterial and viral infections (Baumgarth et al., 2000; Boes et al., 1998; Briles et al., 1981; Haas et al., 2005; Ochsenbein et al., 1999), and may play a role in a wide variety of diseases, through recognition of self-antigens and binding of cellular debris (Binder and Silverman, 2005). In addition, B1 cells differ functionally from B2 cells in efficiently presenting antigen to T cells (Zhong et al., 2007), and in displaying evidence of tonic signaling (Holodick et al., 2009b; Karras et al., 1997; Wong et al., 2002), in the "resting" state in the absence of specific stimulation. Whereas B1 cells have been considered to be self-renewing and thus self-perpetuating in adult animals (Hayakawa et al., 1986; Kantor et al., 1995), recent evidence suggests that new bone marrow emigrants are continually added to the B1 cell pool (Holodick et al., 2009a).

A subpopulation of CD5-expressing B cells is found in various human tissues, and the number of such CD5+ B cells is expanded in some autoimmune diseases (Burastero et al., 1988; Dauphinee et al., 1988; Plater-Zyberk et al., 1985; Taniguchi et al., 1987). The significance of this is uncertain, however, because it is not clear that CD5 is a durable marker of the B1 cell population across species. Not only is CD5 expressed on B2 cell populations in the human system (including transitional, pre-naive and activated B cells), but in other mammals CD5 is nondiscriminatory (Freedman et al., 1989; Lee et al., 2009; Raman and Knight, 1992; Sims et al., 2005; Wilson and Wilkie, 2007). As a result there has been much controversy regarding whether B1 cells exist at all in Homo sapiens, and if so, how human B1 cells might be characterized. Resolution of this problem is of great importance, because a full understanding of the relationship between B1 cells and diseases ranging from autoimmune dyscrasias to lymphoid malignancies depends on elucidating identifying features that will allow human B1 cells to be readily enumerated and functionally evaluated in clinical situations.

SUMMARY OF THE INVENTION

To address this long felt need, various phenotypically defined populations from umbilical cord and adult peripheral blood were screened for key characteristics of the well-studied murine B1 cell population, specifically, spontaneous IgM secretion, efficient T cell stimulation, and tonic intracellular signaling. Using these functional criteria, the present inventors have identified the phenotypic profile for human B1 cells as CD20+CD27+CD43+. In addition, the inventors have further identified two distinct subpopulations of the population of human B1 cells on the basis of CD11b expression, and have identified significant functional differences in these subpopulations.

Accordingly, the invention provides an isolated population of human natural immunoglobulin-producing B1 lymphocytes, wherein the B1 lymphocytes are characterized as co-expressing surface biomarkers CD20, CD43 and CD27.

In addition, the invention also provides a separate population of human natural immunoglobulin-producing B1 lymphocytes, wherein the B1 lymphocytes are characterized as co-expressing surface biomarkers CD20, CD43 and CD27 and as not co-expressing surface biomarker CD11b.

A method is also provided of isolating human natural immunoglobulin-producing B1 lymphocytes from a blood sample comprising isolating B lymphocytes from the sample that co-express surface biomarkers CD20, CD43 and CD27.

A method is also provided of isolating human natural immunoglobulin-producing B1 lymphocytes from a blood sample comprising isolating B lymphocytes from the sample that co-express surface biomarkers CD20, CD43, CD27 and CD11b.

The invention also provides a method for diagnosing a B1 cell disorder in a patient, the method comprising determining the level of B lymphocytes in the patient that co-express surface biomarkers CD20, CD43 and CD27, wherein an elevation as compared to a control of B lymphocytes co-expressing surface biomarkers CD20, CD43 and CD27 indicates that the patient has a B1 cell disorder.

The invention also provides method for diagnosing a B1 cell disorder in a patient, the method comprising determining the level of B lymphocytes in the patient that co-express surface biomarkers CD20, CD43, CD27 and CD11, wherein an elevation as compared to a control of B lymphocytes co-expressing surface biomarkers CD20, CD43, CD27 and CD11b indicates that the patient has a B1 cell disorder.

The invention also provides a method of determining the prognosis of a patient having a B1 cell disorder comprising determining the level of B lymphocytes in the patient that co-express surface biomarkers CD20, CD43 and CD27, wherein an elevation of B lymphocytes co-expressing surface biomarkers CD20, CD43 and CD27 as compared to a control indicates a poor prognosis of the B1 cell disorder in the patient.

A method is also provided of determining the prognosis of a patient having a B1 cell disorder comprising determining the level of B lymphocytes in the patient that co-express surface biomarkers CD20, CD43, CD27 and CD11b, wherein an elevation of B lymphocytes co-expressing surface biomarkers CD20, CD43, CD27 and CD11b as compared to a control indicates a poor prognosis of the B1 cell disorder in the patient.

Methods of treatment are also provided by the invention. A method is provided of treating a patient having a B1 cell disorder comprising administering to the patient an amount of an agent or agents effective to decrease B lymphocytes co-expressing surface biomarkers CD20, CD43 and CD27. Also provided is a method of treating a patient having a B1 cell disorder comprising depleting the CD20+CD27+CD43+ cell population of the patient extracorporeally.

The methods also provides agents and compositions. An agent is provided that binds to (i) CD20 and CD43, (ii) CD20 and CD27, (iii) CD43 and CD27, (iv) CD11b and CD20, (v) CD11b and CD43, or (vi) CD11b and CD27. A combination of two agents is provided, each of which binds to a different combination of (i) CD20 and CD43, (ii) CD20 and CD27, (iii) CD43 and CD27, (iv) CD11b and CD20, (v) CD11b and CD43, and (vi) CD11b and CD27. A pharmaceutical composition is provided comprising the agent or combination of agents described hereinabove.

The invention further provides useful kits. A kit comprising one or more agents that can be used to detect, quantify or remove B lymphocytes co-expressing CD20, CD27 and CD43 is provided, and comprises instructions for the use of the one or more agents to detect, quantify or remove B lymphocytes co-expressing CD20, CD27 and CD43. A kit comprising one or more agents is also provided that can be used to detect, quantify or remove B lymphocytes co-expressing CD20, CD27, CD43 and CD11, and instructions for the use of the one or more agents to detect, quantify or remove B lymphocytes co-expressing CD20, CD27, CD43 and CD11b.

A method is also provided for treating an autoimmune disease mediated by B1 lymphocytes in a subject without reducing other B cell function in the subject comprising reducing the level of CD20+CD27+CD43+CD11b+ cells in the subject, thereby treating the autoimmune disease.

Assays for identifying therapeutic and/or active agents are also provided. As such, a method is provided for identifying an agent as a candidate for treating a B1 lymphocyte-mediated autoimmune disease comprising contacting (i) a CD20+CD27+CD43+CD11b+ cell and (ii) a CD20+CD27+CD43+CD11b− cell with the agent, wherein if the agent kills the CD20+CD27+CD43+CD11b+ cell but does not kill the CD20+CD27+CD43+CD11b− cell, then the agent is a candidate for treating a B1 lymphocyte-mediated autoimmune disease.

Also, the present invention is directed to an isolated population of human natural immunoglobin-producing B1 lymphocytes, wherein the B1 lymphocytes are characterized as co-expressing surface biomarkers CD20, CD43 and CD27.

The present invention is also directed to a method of isolating human natural immunoglobin-producing B1 lymphocytes from a blood sample comprising isolating B lymphocytes from the sample that co-express surface biomarkers CD20, CD43 and CD27.

In addition, the present invention is directed to a method for diagnosing a B1 cell disorder in a patient, the method comprising determining the level of B lymphocytes co-expressing surface biomarkers CD20, CD43 and CD27 in the patient, wherein an elevation of B lymphocytes co-expressing surface biomarkers CD20, CD43 and CD27 indicatives that the patient has a B1 cell disorder.

The present invention is also directed to a method of determining the prognosis of a patient having a B1 cell disorder comprising determining the level of B lymphocytes co-expressing surface biomarkers CD20, CD43 and CD27 in the patient, wherein an elevation of B lymphocytes co-expressing surface biomarkers CD20, CD43 and CD27 indicatives poor prognosis of the B1 cell disorder in the patient.

Still further, the present invention is directed to a method for treating a patient having a B1 cell disorder comprising administering to the patient an amount of an agent effective to decrease B lymphocytes co-expressing surface biomarkers CD20, CD43 and CD27 in the patient.

The present invention is also directed to a method for treating a patient having a B1 cell disorder comprising depleting the CD20+CD27+CD43+ cell population in the patient extracorporeally.

In addition, the present invention is directed to an agent that that binds to (i) CD20 and CD43, (ii) CD20 and CD27, or (iii) CD43 and CD27.

The present invention is also directed to a combination of two agents, each of which binds to a different combination of (i) CD20 and CD43, (ii) CD20 and CD27, and (iii) CD43 and CD27.

The present invention is also directed to a pharmaceutical composition comprising the agent or combination of agents above.

Lastly, the present invention is directed to a kit comprising one or more agents that can be used to detect, quantify or remove B lymphocytes co-expressing CD20, CD27 and CD43, and instructions for the use of the one or more agents to detect, quantify or remove B lymphocytes co-expressing CD20, CD27 and CD43.

Additional objects of the invention will be apparent from the description which follows.

DETAILED DESCRIPTION OF THE INVENTION

Figures 1A, 1B, 1C, 1D:
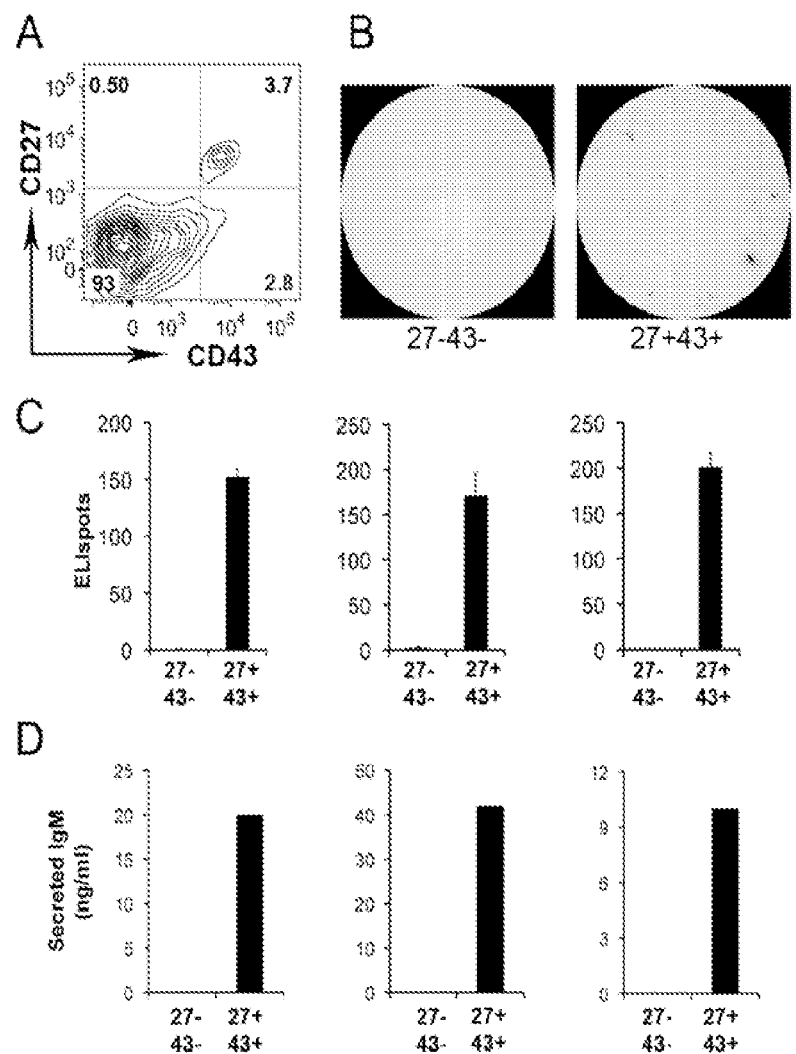
FIG. 1. Umbilical cord blood CD20+CD27+CD43+ B cells spontaneously secrete IgM. A) Umbilical cord blood mononuclear cells were stained with immunofluorescent antibodies and evaluated by flow cytometry. Expression of CD27 and CD43 by CD20+ cells is displayed. Results shown represent one of 13 separate cord blood samples. B) Sort-purified CD20+CD27−CD43− (27−43−) and CD20+CD27+CD43+ (27+43+) cord blood B cells were plated at 1×10$^4$ cells per well, incubated for 3 hours at 37° C., and analyzed for IgM secretion by ELISPOT. Images shown are representative of three separate experiments on three different cord blood samples each done in triplicate. C) Enumeration of ELISPOT results displayed as mean values for triplicate wells with lines indicating standard errors of the means. Each bar graph indicates an individual experiment on a separate cord blood sample. D) Sort-purified CD20+CD27−CD43− and CD20+CD27+CD43+ cord blood B cells were cultured for 5 days after which supernatants were evaluated for secreted IgM by ELISA. Each bar graph indicates an individual experiment on a separate cord blood sample.

In accordance with the present invention, B1 lymphocytes are defined as B lymphocytes that co-express surface biomarkers CD20, CD43 and CD27, and can be additionally distinguished based on CD11b expression.

The invention provides an isolated population of human natural immunoglobulin-producing B1 lymphocytes, wherein the B1 lymphocytes are characterized as co-expressing surface biomarkers CD20, CD43 and CD27, and, optionally CD11b.

In a preferred embodiment, the isolated population of human natural immunoglobulin-producing B1 lymphocytes are characterized as co-expressing surface biomarker CD11b. In a further embodiment, the isolated population of human natural immunoglobulin-producing B1 lymphocytes are also characterized as co-expressing surface biomarker CD14 and/or surface biomarker CD11c. In an embodiment of the described populations, each population is substantially free of B lymphocytes that do not co-express surface biomarker CD11b. In an embodiment of the described populations, each population is substantially free of B lymphocytes that do not co-express surface biomarker CD14 and/or surface biomarker CD11c.

The invention also provides a separate population of human natural immunoglobulin-producing B1 lymphocytes, wherein the B1 lymphocytes are characterized as co-expressing surface biomarkers CD20, CD43 and CD27 and as not co-expressing surface biomarker CD11b. In a further embodiment, the isolated population of human natural immunoglobulin-producing B1 lymphocytes not co-expressing surface biomarker CD11b are also characterized as also not co-expressing surface biomarker CD14 and/or surface biomarker CD11c. In an embodiment of the population of B1 lymphocytes characterized as co-expressing surface biomarkers CD20, CD43 and CD27 and as not co-expressing surface biomarker CD11b, the population is substantially free of B lymphocytes that do co-express surface biomarker CD11b.

In an embodiment of each of the above-described populations, the isolated B1 lymphocytes are obtained from umbilical cord blood. In an embodiment of the described populations, the isolated B1 lymphocytes are obtained from peripheral blood.

In an embodiment of each of the above-described populations, each population is substantially free of B lymphocytes that do not co-express surface biomarkers CD20, CD43 and CD27.

In an embodiment of each of the above-described populations, the isolated B1 lymphocytes exhibit spontaneous IgM secretion, efficient T cell stimulation and tonic intracellular signaling.

In an embodiment of each of the above-described populations, the isolated B1 lymphocytes do not express CD138.

In an embodiment of each of the above-described populations, the isolated B1 lymphocytes express ZAP-70 and ILT3.

In accordance with the compositions and methods of the present invention, the B1 lymphocytes can be isolated from a blood sample containing B lymphocytes including, for example, umbilical cord or peripheral blood. In the preferred embodiment, the B1 lymphocytes are isolated from peripheral blood. B lymphocytes expressing these markers can be isolated and purified using the known procedures such as those described in the Experimental Details Section below. By way of example, mononuclear cells can be obtained by density gradient separation for instance using lymphocyte separation medium (Celigro). Thereafter, the B lymphocytes expressing surface biomarkers CD20, CD43 and CD27 and which are either CD11b+ or CD11b− can be sort purified using an Influx instrument (BD) using known techniques. The purity of the isolated lymphocyte populations can be determined, for example, by flow cytometric analysis on an LSR-II instrument (BD). The population of purified B lymphocytes co-expressing surface biomarkers CD20, CD43 and CD27 are substantially free of B lymphocytes that do not display co-express surface biomarkers CD20, CD43 and CD27. Moreover, the population that expresses CD11b is substantially free of B lymphocytes that do not display CD11b, and the population that does not express CD11b is substantially free of B lymphocytes that do display CD11b. The populations can be further sorted as CD14+ and/or CD11c+, and also as CD14− and/or CD11c−.

In accordance with the composition and method of the present invention, the isolated B1 lymphocytes are also characterized as exhibiting spontaneous IgM secretion (for example, as determined by the ELISPOT assay), efficient T cell stimulation (for example, as determined by allogeneic stimulation) and tonic intracellular signaling (for example, as determined by phosphoflow analysis), as described in detail in the Experimental Details Section below. In another embodiment, the isolated B1 lymphocytes do not express CD138. In yet another embodiment, the isolated B1 lymphocytes express ZAP-70 and ILT3. In yet another embodiment, the isolated B1 lymphocytes express one or more of CD69, CD70 and CD80, and preferably CD69, CD70 and CD80. In yet another embodiment, the isolated B1 lymphocytes express one or more of CD14 and CD11c. In yet another embodiment, the isolated B1 lymphocytes which are CD11b+ do not express CD5.

The above-described populations have various uses, including use for eliciting production of antibodies thereto (for example in non-human mammals).

The invention also provides a method of isolating human natural immunoglobulin-producing B1 lymphocytes from a blood sample comprising isolating B lymphocytes from the sample that co-express surface biomarkers CD20, CD43 and CD27.

The invention further provides a method of isolating human natural immunoglobulin-producing B1 lymphocytes from a blood sample comprising isolating B lymphocytes from the sample that co-express surface biomarkers CD20, CD43, CD27 and CD11b. In an embodiment, the cells co-express surface biomarkers CD11c and/or CD14. In an embodiment of the methods, the B1 lymphocytes are substantially free of B lymphocytes that do not co-express surface biomarker CD11b. In an embodiment of the methods, the B1 lymphocytes are substantially free of B lymphocytes that do not co-express surface biomarkers CD11c and/or CD14.

The invention further provides a method of isolating human natural immunoglobulin-producing B1 lymphocytes from a blood sample comprising isolating B lymphocytes from the sample that co-express surface biomarkers CD20, CD43, CD27 and which do not express CD11b on their surface. In an embodiment, the cells also do not co-express surface biomarkers CD11c and/or CD14.

In an embodiment of each of the above-described methods, the sample is umbilical cord blood or peripheral blood.

In an embodiment of each of the above-described methods, the B1 lymphocytes are substantially free of B lymphocytes that do not co-express surface biomarkers CD20, CD43 and CD27.

In an embodiment of each of the above-described methods, the B1 lymphocytes exhibit spontaneous IgM secretion, efficient T cell stimulation and tonic intracellular signaling.

In an embodiment of each of the above-described methods, the B1 lymphocytes do not express CD138.

In an embodiment of each of the above-described methods, the B1 lymphocytes express ZAP-70 and ILT3. In an embodiment the B1 lymphocytes are CD70−.

The invention also provides diagnostic methods. A method is also provided for diagnosing a B1 cell disorder in a patient, the method comprising determining the level of B lymphocytes in the patient that co-express surface biomarkers CD20, CD43 and CD27, wherein an elevation as compared to a control of B lymphocytes co-expressing surface biomarkers CD20, CD43 and CD27 indicates that the patient has a B1 cell disorder.

A method is also provided for diagnosing a B1 cell disorder in a patient, the method comprising determining the level of B lymphocytes in the patient that co-express surface biomarkers CD20, CD43, CD27 and CD11, wherein an elevation as compared to a control of B lymphocytes co-expressing surface biomarkers CD20, CD43, CD27 and CD11b indicates that the patient has a B1 cell disorder.

If the level of B1 lymphocytes is greater than a normal control, then the elevated B1 cells indicatives a B1 cell disorder is or may be present in the patient or subject. The control is preferably a level of B lymphocytes co-expressing biomarkers CD20, CD43 and CD27 and, optionally, additionally CD11b, that is determined from a patient or group of patients that do not have the B1 cell disorder. With respect to the B lymphocytes co-expressing surface biomarkers CD20, CD43 and CD27, and, optionally, additionally CD11b, it is also within the confines of the invention that the function of such B1 lymphocytes can be determined. In certain embodiments of the invention, an abnormal function of B1 lymphocytes may be considered diagnostic of a particular B1 cell disorder, in comparison to B1 lymphocytes from a control (e.g., a subject or patient or group of subjects or patients having normal, functional B1 lymphocytes).

The invention also provides a method of determining the prognosis of a patient having a B1 cell disorder comprising determining the level of B lymphocytes in the patient that co-express surface biomarkers CD20, CD43 and CD27, wherein an elevation of B lymphocytes co-expressing surface biomarkers CD20, CD43 and CD27 as compared to a control indicates a poor prognosis of the B1 cell disorder in the patient.

The invention also provides a method of determining the prognosis of a patient having a B1 cell disorder comprising determining the level of B lymphocytes in the patient that co-express surface biomarkers CD20, CD43, CD27 and CD11b, wherein an elevation of B lymphocytes co-expressing surface biomarkers CD20, CD43, CD27 and CD11b as compared to a control indicates a poor prognosis of the B1 cell disorder in the patient.

The present invention is also directed to a method of determining the prognosis of a patient having a B1 cell disorder comprising determining the level of B lymphocytes co-expressing surface biomarkers CD20, CD43 and CD27 and, optionally, additionally CD11b, in the patient, wherein an elevation of B lymphocytes co-expressing surface biomarkers CD20, CD43 and CD27 and, optionally, additionally CD11b, indicates poor prognosis of the B1 cell disorder in the patient. In accordance with this method, the appropriate blood sample can be obtained from the patient, and B lymphocytes co-expressing biomarkers CD20, CD43 and CD27 and, optionally, additionally CD11b, can be isolated and quantified. If the level of B1 lymphocytes is greater than a control, then the elevated B1 cells indicates poor prognosis of a B1 cell disorder in the patient or subject. In connection with prognosis, the control may be a level of B lymphocytes co-expressing biomarkers CD20, CD43 and CD27 and, optionally, additionally CD11b, from a patient or group of patients that do not have the B1 cell disorder. Alternatively, the control may be the level of B lymphocytes co-expressing biomarkers CD20, CD43 and CD27 and, optionally, additionally CD11b, that was taken from the same patient at some earlier time such as, for example, before the initiation of therapy. In this regard, it is within the confines of the present invention that the prognosis can be used to determine whether a given therapy or treatment of a patient is successful and should be continued, or is unsuccessful so that alternative therapy or therapies should be considered. With respect to the B lymphocytes co-expressing surface biomarkers CD20, CD43 and CD27, and, optionally, additionally CD11b, it is also within the confines of the invention that the function of such B1 lymphocytes can be determined. In certain embodiments of the invention, an abnormal function of B1 lymphocytes may be considered prognostic of a particular B1 cell disorder, in comparison to B1 lymphocytes from a control (e.g., a patient or group of patients having normal, functional B1 lymphocytes). Alternatively, a raise or lowering of abnormal B1 lymphocyte function in the same patient by be indicative of an unsuccessful or successful course of treatment.

The invention also provides a method of treating a patient having a B1 cell disorder comprising administering to the patient an amount of an agent or agents effective to decrease B lymphocytes co-expressing surface biomarkers CD20, CD43 and CD27. In an embodiment, the agent or agents are effective to decrease B lymphocytes co-expressing surface biomarkers CD20, CD43, CD27 and CD11b.

The invention also provides a method of treating a patient having a B1 cell disorder comprising depleting the CD20+CD27+CD43+ cell population of the patient extracorporeally. In an embodiment, the method depletes the CD20+CD43+CD27+CD11b+ cell population of the patient extracorporeally.

In an embodiment of the methods, the B1 cell disorder is an autoimmune disease. In an embodiment, the autoimmune disease is systemic lupus erythematosus, rheumatoid arthritis, multiple sclerosis, immune thrombocytopenia purpura, primary Sjogren's syndrome, juvenile arthritis, primary antiphospholipid syndrome, Graves' disease, myasthenia gravis, chronic hepatitis, Crohn's disease or type 1 diabetes. In an embodiment, the autoimmune disease is systemic lupus erythematosus.

In an embodiment of the methods, the B1 cell disorder is chronic lymphocytic leukemia, hairy cell leukemia, prolymphocytic leukemia, or non-Hodgkin's lymphoma. In an embodiment, the B1 cell disorder is chronic lymphocytic leukemia.

In an embodiment of the methods, the agent binds to CD20, CD43, and CD27.

In an embodiment of the methods, the agent also binds to CD11b.

In an embodiment of the methods, the agent comprises one or more agents that bind to at least two of CD20, CD43, CD27 and CD11b.

In an embodiment of the methods, the agent or agents is an antibody or antigen-binding fragment of an antibody, an aptamer or a peptide.

In an embodiment of the methods, the agent is an antibody or antigen-binding fragment of an antibody or the agents are antibodies and/or antigen-binding fragments of antibodies.

In an embodiment of the methods, the agent is a bi-specific antibody, bi-specific antigen-binding fragment of an antibody, or the agents are bispecific antibodies and/or bi-specific antigen-binding fragments of antibodies. In an embodiment, the bi-specific antibody, antibodies or antigen binding fragment(s) are directed to two of CD20, CD43, CD27 and CD11b.

In an embodiment of the methods, the antibody is or antibodies are monoclonal or the antigen binding fragment(s) are fragment(s) of monoclonal antibodies.

In an embodiment of the methods, the agent is bi-specific antibody or antibodies that hind to one or more of (i) CD20 and CD43, (ii) CD20 and CD27, (iii) CD43 and CD27 (iv) CD11b and CD20, (v) CD11b and CD43, or (vi) CD11b and CD27.

In an embodiment of the methods, the agent is conjugated with a toxin, cytotoxin, radioligand, radionuclide, or chemotherapeutic, or agents are each conjugated, independently, with a toxin, cytotoxin, radioligand, radionuclide, or chemotherapeutic.

In accordance with the treatment of the B1 cell disorder, the agent is an amount effective to treat the disease. As used herein, "treat" or "treating" can be the reduction, attenuation or elimination of a symptom or condition associated with B1 cell disorder and/or a reduction, attenuation or elimination of the underlying B1 cell disorder as well.

The agent or agents used in accordance with the present invention can be one or more antibodies, aptamers or peptides, or T lymphocytes or natural killer (NK) cells reactive with a B-cell specific molecule (herein called "chimeric antigen receptors") or other bioengineered molecules that can be made to bind to cell surface membrane antigens on cells, and methods for the preparation of these agents are well know to the skilled artisan. In the preferred embodiment, the agents are antibodies. In this regard, it is within the confines of the present invention that the agent may be a bi-specific antibody that binds to two cell surface membrane antigens. Preferably, the agent is a bi-specific antibody that binds to (i) CD20 and CD43, (ii) CD20 and CD27, or (ii) CD43 and CD27, and most preferably is a combination of hi-specific antibodies each of which binds to a different one of (i) CD20 and CD43, (ii) CD20 and CD27, and (ii) CD43 and CD27. It is within the confines of the present invention that the antibodies can be polyclonal or monoclonal antibodies. In addition, the antibodies for use in the present invention can be rodent (e.g., mouse), chimeric, humanized or human antibodies, and are preferably human antibodies.

When more than one agent is used for therapy, the agents may be administered simultaneously or in tandem. It is also within the confines of the present invention that the agent or agents may be conjugated with or attached or bound to a toxin or radioligand. The agent or agents also may be administered in a manner that permit the agent or agents (alone or bound to a toxin or radioligand) to contact the B1 cells in the bone marrow or in the periphery to destroy or kill these cells, and to thereby treat the B1 cell disorder. In this regard, it is contemplated that the agent or agents (alone or bound to a toxin or radioligand) can be administered directly to the blood stream of the patient (e.g., by injection), directly to the bone marrow of the patient, or in conjunction with a bone marrow transplant (e.g., autologous or allogenic bone marrow transplant) in which the agents are present in the bone marrow transplant composition. Still further, it is within the confines of the present invention that the agent or agents can be administered prior to, following, or in combination with other therapeutic treatments for B cell disorders.

The present invention is also directed to a method for treating a patient having a B1 cell disorder comprising depleting the CD20+CD27+CD43+ cell population in the patient extracorporeally such as by plasmapheresis. In this regard, the plasma or blood is removed from the patient, the CD20+ CD27+CD43+ cell population is removed from the blood or plasma, and the plasma or blood lacking the CD20+CD27+ CD43+ cell population is then returned to the patient. Again, as used herein, "treat" or "treating" can be the reduction, attenuation or elimination of a symptom or condition associated with B1 cell disorder and/or a reduction, attenuation or elimination of the underlying B1 cell disorder as well. For plasmapheresis, the plasma can be directly removed from the patient or can be separated from the blood by filtration.

In addition, the present invention provides a pharmaceutical composition that comprises the agent or combination of agents above, together with pharmaceutically acceptable carriers. The formulation of agents such as antibodies, aptamers or peptides, and or T lymphocyte or natural killer cell with a chimeric bispecific receptor is well known to the skilled artisan.

In accordance with the methods for diagnosis, prognosis and treatment, the B1 cell disorder may be, for example, a disease or condition such as an autoimmune disease or a cancer associated with or caused by B cells. In this regard, the autoimmune disease may include systemic lupus erythematosus, rheumatoid arthritis, multiple sclerosis, immune thrombocytopenia purpura, primary Sjogren's syndrome, juvenile arthritis, primary antiphospholipid syndrome, Graves' disease, myasthenia gravis, chronic hepatitis, Crohn's disease or type 1 diabetes, and other known autoimmune diseases associated with B cells. In the preferred embodiment, the autoimmune disease is systemic lupus erythematosus. In terms of B cell cancer, the B1 cell disorder may include cancers such as chronic lymphocytic leukemia, hairy cell leukemia, prolymphocytic leukemia or non-Hodgkin's lymphoma, and is preferably chronic lymphocytic leukemia.

This invention also prpvides agents and combinations of agents. An agent is provided that binds to (i) CD20 and CD43, (ii) CD20 and CD27, (iii) CD43 and CD27, (iv) CD11b and CD20, (v) CD11b and CD43, or (vi) CD11b and CD27. In an embodiment, the agent is for treating an autoimmune disease. In an embodiment, the autoimmune disease is systemic lupus erythematosus, rheumatoid arthritis, multiple sclerosis, immune thrombocytopenia purpura, primary Sjogren's syndrome, juvenile arthritis, primary antiphospholipid syndrome, Graves' disease, myasthenia gravis, chronic hepatitis, Crohn's disease or type I diabetes. In an embodiment, the autoimmune disease is systemic lupus erythematosus.

A combination of two agents is also provided, each of which agents binds to a different combination of (i) CD20 and CD43, (ii) CD20 and CD27, (iii) CD43 and CD27, (iv) CD11b and CD20, (v) CD11b and CD43, and (vi) CD11b and CD27. In an embodiment, the combination of two agents is for treating an autoimmune disease. In an embodiment, the autoimmune disease is systemic lupus erythematosus, rheumatoid arthritis, multiple sclerosis, immune thrombocytopenia purpura, primary Sjogren's syndrome, juvenile arthritis, primary antiphospholipid syndrome, Graves' disease, myasthenia gravis, chronic hepatitis, Crohn's disease or type 1 diabetes. In an embodiment, the autoimmune disease is systemic lupus erythematosus.

Compositions and pharmaceutical compositions comprsing the agent(s) or combinations of agents described herein are also providced. In a preferred embodiment, a pharmaceutical composition is provided comprising the agent or combination of agents described hereinabove.

Kits are also provided bvy the present invention. A kit is provided comprising one or more agents that can be used to detect, quantify or remove B lymphocytes co-expressing CD20, CD27 and CD43, and instructions for the use of the one or more agents to detect, quantify or remove B lymphocytes co-expressing CD20, CD27 and CD43. Another kit comprising one or more agents is provided that can be used to detect, quantify or remove B lymphocytes co-expressing CD20, CD27, CD43 and CD11, and instructions for the use of the one or more agents to detect, quantify or remove B lymphocytes co-expressing CD20, CD27, CD43 and CD11b.

For diagnostic purposes, the kits preferably would include one or more agents that can be used to detect or quantify B lymphocytes co-expressing CD20, CD27 and CD43, and CD11b if appropriate, and instructions for the use of the one or more agents to detect or quantify lymphocytes co-expressing CD20, CD27 and CD43, and CD11b if appropriate. For therapeutic applications, the kit would preferably include one or more agents that can be used to remove B lymphocytes co-expressing CD20, CD27 and CD43, and CD11b if appropriate, and instructions for the use of the one or more agents to remove B lymphocytes co-expressing CD20, CD27 and CD43, and CD11b if appropriate. The one or more agents can include the one or more agents as discussed above.

The invention also provides a method for identifying an agent as a candidate for treating a B1 lymphocyte-mediated autoimmune disease comprising contacting (i) a CD20+CD27+CD43+CD11b+ cell and (ii) a CD20+CD27+CD43+CD11b− cell with the agent, wherein if the agent kills the CD20+CD27+CD43+CD11b+ cell but does not kill the CD20+CD27+CD43+CD11b− cell, then the agent is a candidate for treating a B1 lymphocyte-mediated autoimmune disease. In an embodiment, the cells are obtained from a human. In an embodiment the agent is a small molecule, an organic molecule of 2000 daltons or less, an antibody, a fragment of an antibody or a peptide.

In an embodiment of the methods described herein, the subject or patient is a human.

All combinations of the various elements described herein are within the scope of the invention unless otherwise indicated herein or otherwise clearly contradicted by context.

This invention will be better understood from the Experimental Details which follow. However, one skilled in the art will readily appreciate that the specific methods and results discussed are merely illustrative of the invention as described more fully in the claims which follow thereafter.

Experimental Details 1

Materials and Methods

Donors and Samples.

Adult peripheral blood samples were obtained by venipuncture of adult volunteers after obtaining informed consent in accordance with the Declaration of Helsinki. Additional samples in the form of leukopacks were obtained from the New York Blood Center on the day of donation. Anonymous umbilical cord blood samples were obtained from the Tissue Donation Program at The Feinstein Institute for Medical Research. This study was approved by, and all samples were obtained in accordance with, the Institutional Review Board of the North Shore-LIJ Health System.

Processing.

All samples were treated in a similar manner and processed promptly upon receipt. Mononuclear cells were obtained by density gradient separation using lymphocyte separation medium (Cellgro). Except as otherwise noted, mononuclear cells were then washed and resuspended in RPMI 1640 (Cellgro) containing 10% fetal calf serum plus 2 mM L-glutamine, 10 mM HEPES (pH 7.25), 100 U/ml penicillin and 100 µg/ml streptomycin.

B Cell Enrichment and Naïve CD4 T Cell Isolation.

For some experiments B cells were enriched by CD19 positive selection using the EasySep Human CD19+ B Cell magnetic bead selection kit (StemCell Technologies) according to the manufacturer's instructions. Naïve CD4+ T cells were isolated using the EasySep Human Naïve CD4+ T Cell magnetic bead selection kit (StemCell Technologies) according to the manufacturer's instructions.

Flow Cytometry Analysis and Cell Sorting.

Enriched B cells and mononuclear cells were sort-purified on an Influx instrument (BD) after immunofluorescent staining, as described in Results. The purity of isolated lymphocyte populations was determined by flow cytometric analysis on an LSR-II instrument (BD).

ELISPOT.

Immunoglobulin secretion was determined by ELISPOT assay as previously described (Tumang et al., 2005), using MultiScreen-IP plates (Millipore) coated with goat anti-human IgM (Southern Biotech), and blocked with 5% bovine serum albumin (Sigma). In brief, 10,000 sort-purified B cells were cultured in 100 µl RPMI medium (supplemented as above) for 3 hours at 37° C., after which plates were treated with alkaline phosphatase-conjugated anti-human IgM antibody (Southern Biotech) and developed with 5-bromo-4-chloro-3-indoyl phosphate/p-NBT chloride substrate (KPL). Immunoglobulin secreting cells were enumerated with Phoretix Expresson software (NonLinear Dynamics) after plates were scanned.

ELISA.

Immunoglobulin secretion was determined by ELISA assay, as previously described (Hastings et al., 2006). In brief, sort-purified B cells were cultured for 5 days at 1×106 per ml in RPMI medium (supplemented as above). Supernatants were evaluated using anti-IgM coated plates (Bethyl Laboratories) and concentrations determined with a standard curve.

Allogeneic Stimulation.

Naïve CD4+ T cells were negatively selected using the EasySep human naïve CD4+ T cell magnetic bead selection kit (StemCell Technologies) according to the manufacturer's instructions and were co-cultured at a ratio of 2:1 with sort-purified, irradiated (4000 rads) B cells (50,000) in 0.2 ml in RPMI medium in triplicate wells of 96 well round bottom plates. Cultures were pulsed with 0.75 microcuries [$^3$H]thymidine for the last 8 hours of 5 day cultures and cpm determined by scintillation counting.

Phosphoflow Analysis.

Mononuclear cells were analyzed following phosphatase inhibition, as previously described (Holodick et al., 2009b). In brief, cells were sort-purified and then treated with sodium pervanadate for varying periods of time, after which they were fixed with paraformaldehyde, penneabilized with methanol, and stained for surface antigens and intracellular phosphorylated proteins with specific immunofluorescent antibodies. Flow cytometric analysis was performed using a BD Biosciences LSR II.

Single Cell Immunoglohulin Sequencing.

Individual cells were sort-purified onto a 48-well Ampligrid (Advalytix) and immunoglobulin sequences were PCR-amplified in a semi-nested approach as previously described (Holodick et al., 2009a), using primers designed for human immunoglobulin gene transcripts (Wang and Stollar, 2000). Products were sequenced (Genewiz) and sequences analyzed using the International ImMunoGeneTics Information System (IMGT).

Reagents.

Sodium orthovanadate was obtained from MP Biomedicals; one step per and gel extraction kits were obtained from Qiagen; LPS was obtained from Sigma; CpG was obtained from lnvitrogen; and fluorescently labeled antibodies (anti-CD20-APC-Cy7, anti-CD27-V450, anti-CD43-FITC, anti-phospho-PLC-gamma-2-A647, and anti-phospho-Syk-A647) were obtained from BD Biosciences.

Results I

In the murine system, B1 cell progenitors are more abundant in fetal as opposed to adult hematopoietic tissues, and B1 cells emerge before the bulk of B2 cell production occurs (Montecino-Rodriguez et al., 2006). Following this paradigm, umbilical cord blood specimens were first examined for spontaneous IgM secretion by ELISPOT assay, which were used for initial screening, and then looked for efficient T cell stimulation and tonic intracellular signaling. B cells were isolated that were CD20+ to avoid CD19+CD20-plasmablasts.

Umbilical Cord Blood CD20+CD27+CD43+ B Cells Spontaneously Secrete IgM

Initially CD20+ B cells were sort-purified from umbilical cord blood samples and then tested for IgM secretion in 3 hour ELISPOT assays. It was found that unstimulated cord blood B cells spontaneously generated IgM-containing ELISPOTs (data not shown). To phenotypically characterize the immunoglobulin-secreting population, various CD20+ cord blood populations defined by known B cell surface antigens were examined. Among these populations a small subset of CD27+ cells was unexpectedly identified, ranging from 3-11 percent of CD20+ B cells. Similar numbers of CD27+ cord blood B cells were detected by a variety of different anti-CD27 immunofluorescent reagents (data not shown), and expression of CD27 mRNA coincident with expression of CD27 surface antigen was verified by real-time PCR conducted on sort-purified CD20+CD27+ and CD20+CD27- cord blood cells (data not shown). These CD20+CD27+ cord blood B cells uniquely express CD43, a well-described marker for murine B1 cells (Wells et al., 1994), whereas CD20+CD27- cord blood B cells are CD43- (FIG. 1A). Thus CD20+ cord blood B cells segregate into two populations, CD27+CD43+ (amounting to 6.1%+/−1.1, mean+/−standard error of the mean, n=13), and CD27−CD43− (amounting to 93.9%+/−1.1). Although CD27 has been considered a marker of human memory B cells, it was found that CD27 expression neatly and completely separated cord blood B cells that spontaneously secrete IgM from those that do not, as shown by ELISPOT (FIG. 1B) and ELISA (FIG. 1C) analyses. Thus, a small population of CD20+CD27+CD43+ B cells, amounting on average to less than 10% of total B cells in 13 cord blood samples, is responsible for spontaneous IgM secretion in this tissue.

Umbilical Cord Blood CD20+CD27+CD43+ B Cells Efficiently Stimulate T Cells.

Figure 2:
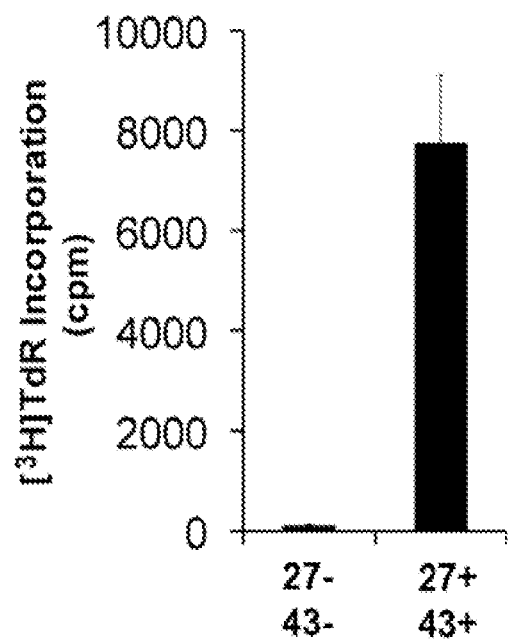
FIG. 2. Umbilical cord blood CD20+CD27+CD43+ B cells efficiently stimulate T cells. Sort purified and irradiated CD20+CD27–CD43– (27–43–) and CD20+CD27+CD43+ (27+43+) cord blood B cells were evaluated for the ability to allogeneically drive T cell proliferation as measured by tritiated thymidine incorporation for 8 hours at the end of 5 day cultures. Data shown are representative of three separate experiments on three different cord blood samples each done in triplicate Mean cpm values are displayed with lines indicating standard errors of the means.

To determine the extent to which IgM-secreting umbilical cord blood B cells express other characteristics derived from murine B1 cell studies, the efficiency of CD4+ T cell allogeneic stimulation produced by irradiated B cell populations were examined, assessed by thymidine incorporation. It was found that CD20+CD27+CD43+ B cells strongly stimulated T cell proliferation over a 5 day period, whereas CD20+CD27−CD43− B cells had little effect (FIG. 2). Thus, not only do CD20+CD27+CD43+ B cells efficiently stimulate T cells, but this functional characteristic is completely restricted to the CD27+CD43+ B cell population.

Umbilical cord blood CD20+CD27+CD43+ B cells exhibit tonic intracellular signaling.

Figures 3A, 3B, 3C, 3D:
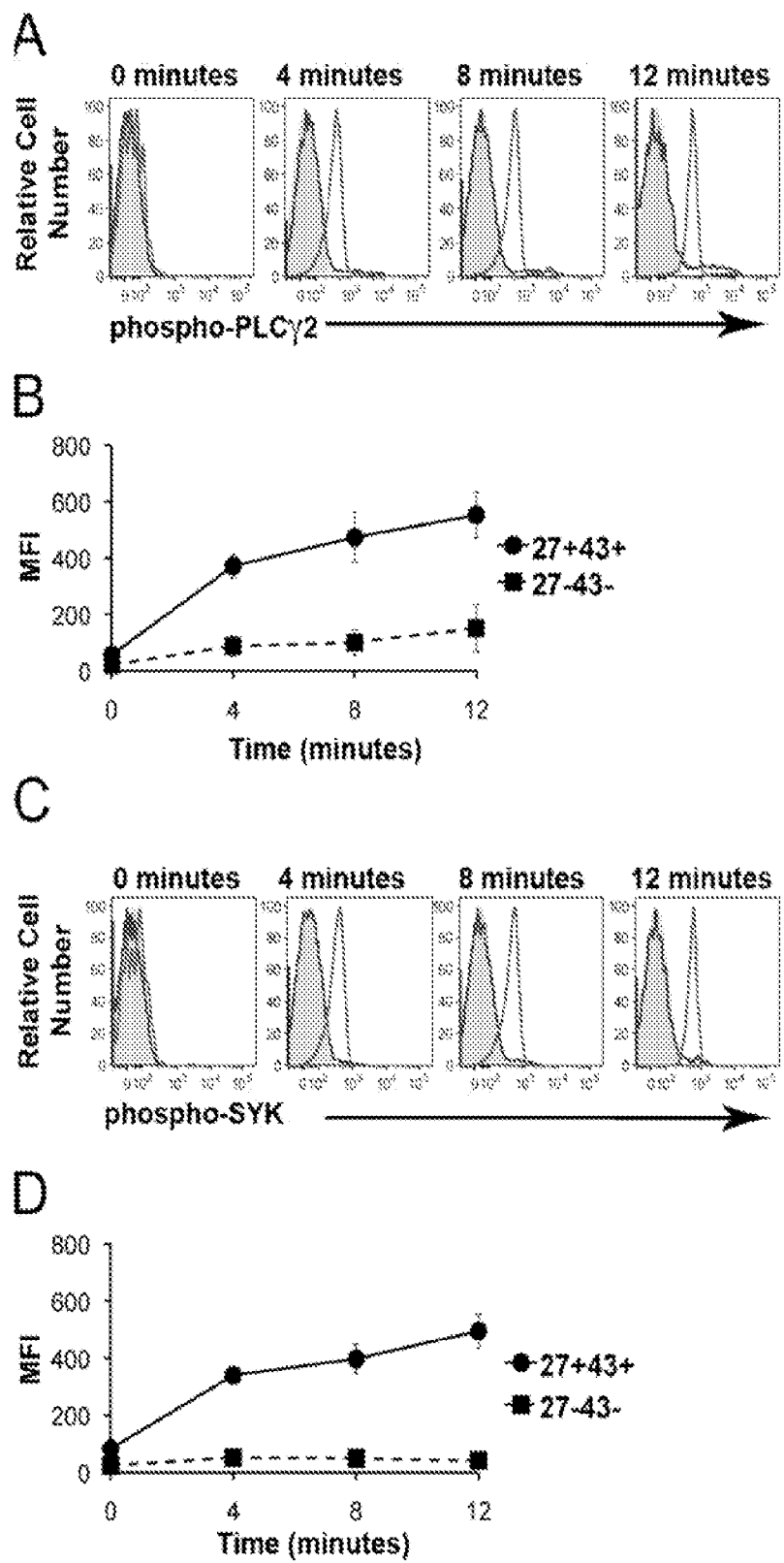
FIG. 3. Umbilical cord blood CD20+CD27+CD43+ B cells exhibit tonic intracellular signaling. A) Cord blood mononuclear cells were evaluated for phosphorylation of PLC-γ2 by intracellular staining after phosphatase inhibition. Cells were unexposed (0) or were exposed to pervanadate for 4, 8, and 12 minutes and then fixed, permeabilized and stained for surface antigens and pPLC-γ2 with specific immunofluorescent antibodies. Histograms show fluorescence produced by isotype control antibody (in solid gray) and by anti-pPLC-γ2 for CD20+CD27–CD43– (27–43–) cells (curve over gray area) and for CD20+CD27+CD43+ (27+43+) cells (curve to right of gray area). Because isotype control antibody staining by "fluorescence minus one" did not vary between the two cell populations under study, only a single control tracing is shown. Results for one of 3 comparable experiments is shown. B) Mean values of MFI are shown (with lines indicating standard errors of the means) for intracellular pPLC-γ2 staining at various time points from 3 separate umbilical cord blood samples. C) Cord blood mononuclear cells were evaluated for phosphorylation of Syk by intracellular staining after phosphatase inhibition. Cells were unexposed (0) or were exposed to pervanadate for 4, 8, and 12 minutes and then fixed, permeabilized and stained for surface antigens and pSyk with specific immunofluorescent antibodies. Histograms show fluorescence produced by isotype control antibody (in solid gray) and by anti-pSyk for CD20+CD27–CD43– (27–43–) cells (curve over gray area) and for CD20+CD27+CD43+ (27+43+) cells (curve to right of gray area). Results for one of 3 comparable experiments is shown. D) Mean values of MFI are shown (with lines indicating standard errors of the means) for intracellular pSyk staining at various time points from 3 separate umbilical cord blood samples.

To further evaluate the extent to which IgM-secreting, T cell-stimulating umbilical cord blood B cells express other murine B1 cell characteristics, tonic intracellular signaling was examined by phosphoflow analysis, in which tyrosine phosphorylation of PLC-γ2 and Syk was readily visualized by intracellular immunofluorescent staining after inhibition of phosphatase activity. Untreated B cells showed little evidence of phospho-PLC-γ2 or phospho-Syk. Within minutes of phosphatase inhibition it was found that CD20+CD27+CD43+ B cells expressed substantial levels of phospho-PLC-γ2 and phospho-Syk, which increased further with time, whereas the levels of phospho-PLC-γ2 and phospho-Syk in CD20+CD27−CD43− B cells did not change (FIG. 3). Thus, the small population of CD20+CD27+CD43+ cord blood B cells displays tonic intracellular signaling that is apparent when phosphatase activity is inhibited, whereas the majority of cord blood B cells which are negative for CD27 expression do not.

Umbilical Cord Blood CD20+CD27+CD43+ B Cell Immunoglobulin Expresses Few Mutations.

In the human system, CD27 expression is generally considered to mark memory B cells (Agematsu et al., 2000), which suggests incongruity in the identification of CD27+ B cells in cord blood that is obtained at birth prior to exogenous antigen exposure. To clarify the nature of umbilical cord blood CD20+CD27+CD43+ B cells, the mutational status of immunoglobulin amplified from single cells was examined as described in Materials and Methods. First, the verification of the reliability of this approach by demonstrating, as expected (Klein et al., 1998), that adult CD27+ B cell-derived antibodies contain many more somatic mutations (13.1+/−1.3, mean+/−SEM, n=24 sequences) than adult CD27− B cell antibodies (1.9+/−1.0, n=10 sequences). It was subsequently found that all cord blood B cells express antibodies with low levels of somatic mutation similar to CD27− adult B cells, both CD20+CD27+CD43+ (1.8+/−0.3, n=43 sequences) and CD20+CD27−CD43− (1.9+/−0.4, n=25 sequences) B cells. Thus, among cord blood B cells, CD27 expression does not correlate with increased immunoglobulin mutational status. In sum, cm the basis of spontaneous IgM secretion, efficient T cell stimulation, tonic intracellular signaling, and low level of immunoglobulin somatic mutation, CD20+CD27+CD43+ cord blood B cells appear to fulfill functional criteria for B1 cell status.

Adult peripheral blood CD20+CD27+CD43+ B cells spontaneously secrete IgM.

Figures 4A, 4B, 4C, 4D:
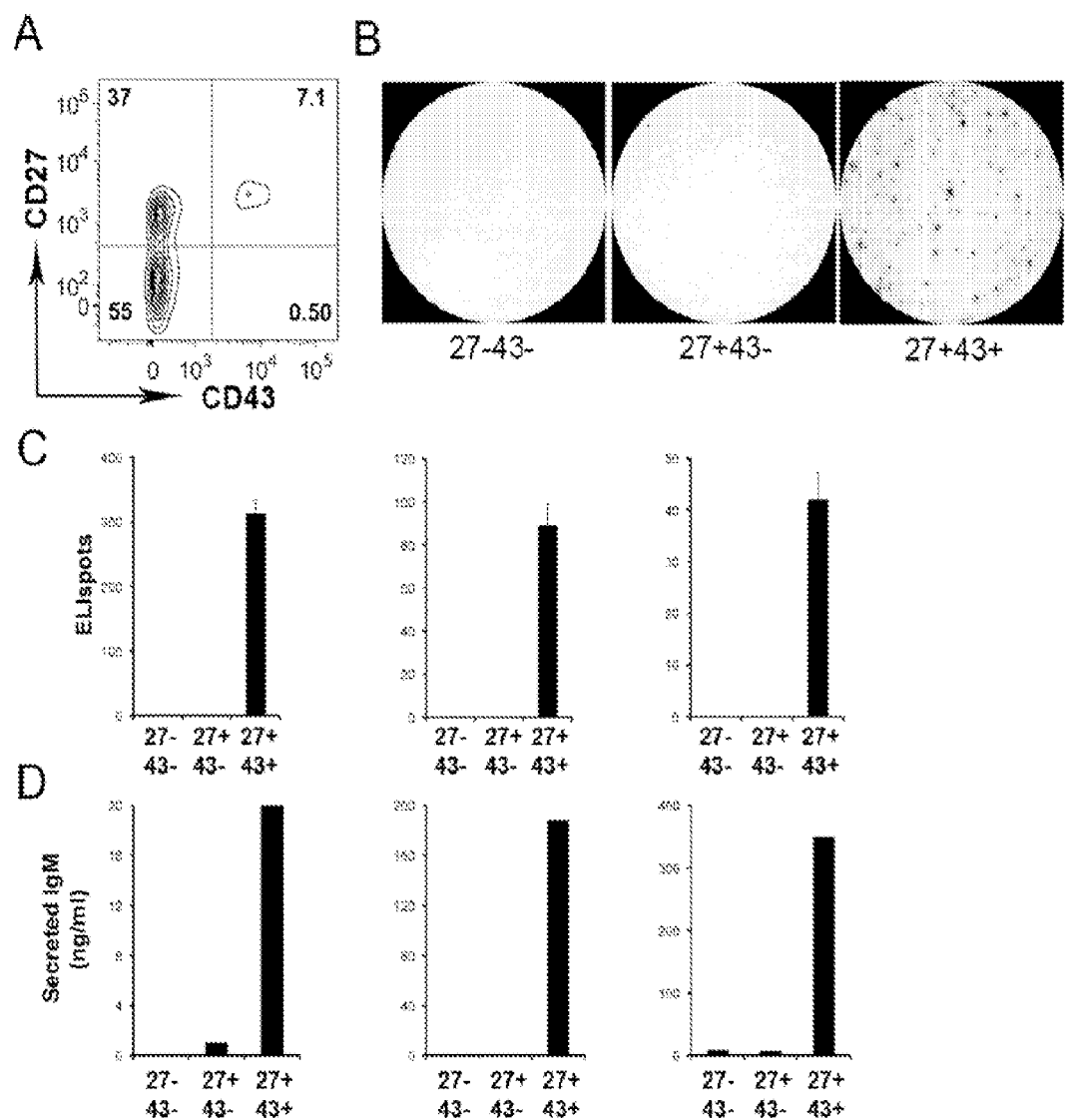
FIG. 4. Adult peripheral blood CD20+CD27+CD43+ B cells spontaneously secrete IgM. A) Adult peripheral blood mononuclear cells were stained with immunofluorescent antibodies and evaluated by flow cytometry. Expression of CD27 and CD43 by CD20+ cells is displayed. Results shown represent one of 25 separate peripheral blood samples. B) Sort-purified CD20+CD27–CD43– (27–43–), CD20+CD27+CD43– (27+43–) and CD20+CD27+CD43+ (27+43+) adult peripheral blood B cells were plated at 1×10$^4$ cells per well, incubated for 3 hours at 37° C., and analyzed for IgM secretion by ELISPOT. Images shown are representative of three separate experiments on three different cord blood samples each done in triplicate. C) Enumeration of ELISPOT results displayed as mean values for triplicate wells with lines indicating standard errors of the means. Each bar graph indicates an individual experiment on a separate adult blood sample. D) Sort-purified CD20+CD27+CD43+, CD20+CD27+CD43– and CD20+CD27–CD43– adult blood B cells were cultured for 5 days after which supernatants were evaluated for secreted IgM by ELISA. Each bar graph indicates an individual experiment on a separate cord blood sample.

Following the strategy outlined above for umbilical cord blood B cells, CD20+ B cells were sort-purified from adult peripheral blood samples and then tested for IgM secretion in 3 hour ELISPOT assays. Unstimulated adult B cells spontaneously generated IgM-containing ELISPOTs, and that IgM secretion segregated with CD27 expression (data not shown). CD43 expression was evaluated and it was found that in adult blood, CD27 and CD43 define 3 distinct populations of CD20+ B cells: CD27+CD43+ (12.7%+/−1.6 of total CD20+ B cells, mean+/−SEM, n=25), CD27+CD43− (19.6%+/−2.2, n=25), and CD27−CD43− (67.7%+/−2.4, n=25) (FIG. 4A), the first of which parallels the phenotype of IgM-secreting cord blood B1 cells. Indeed, when tested by ELISPOT (FIG. 4B) and ELISA (FIG. 4C), it was found that only the small CD20+CD27+CD43+ population from adult blood spontaneously secreted IgM, recapitulating the results obtained with the comparable cord blood B cell population.

Figure 5:
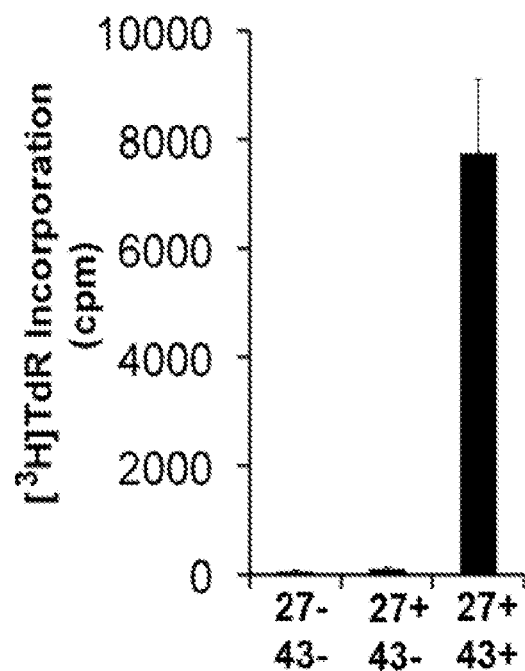
FIG. 5. Adult peripheral blood CD20+CD27+CD43+ B cells efficiently stimulate T cells. Sort-purified and irradiated CD20+CD27–CD43– (27–43–), CD20+CD27+CD43– (27+43–) and CD20+CD27+CD43+ (27+43+) adult peripheral blood B cells were evaluated for the ability to allogeneically drive T cell proliferation as measured by tritiated thymidine incorporation for 8 hours at the end of 5 day cultures. Data shown are shown are representative of three separate experiments on three different cord blood samples each done in triplicate. Mean cpm values are displayed with lines indicating standard errors of the means.

Adult peripheral blood CD20+CD27+CD43+ B cells efficiently stimulate T cells. To determine the extent to which IgM-secreting CD20+CD27+CD43+ adult peripheral blood B cells express other B1 characteristics (and recapitulate the features of cord blood CD20+CD27+CD43+ B cells), the efficiency of allogeneic CD4+ T cell stimulation produced by irradiated B cell populations was examined. CD20+CD27+CD43+ B cells strongly stimulated T cell proliferation, whereas CD20+CD27+CD43− B cells, and CD20+CD27−CD43− B cells, had little effect (FIG. 5). In particular, CD20+CD27+CD43+ B cells exceeded CD20+CD27+CD43− B cells by more than 50-fold in the ability to stimulate T cell proliferation. Thus, in comparison with the bulk of adult peripheral B cells that do not express CD43, only the small population of CD20+CD27+CD43+ B cells efficiently stimulates T cells.

Adult Peripheral Blood CD20+CD27+CD43+ B Cells Exhibit Tonic Intracellular Signaling.

Figures 6A, 6B, 6C, 6D:
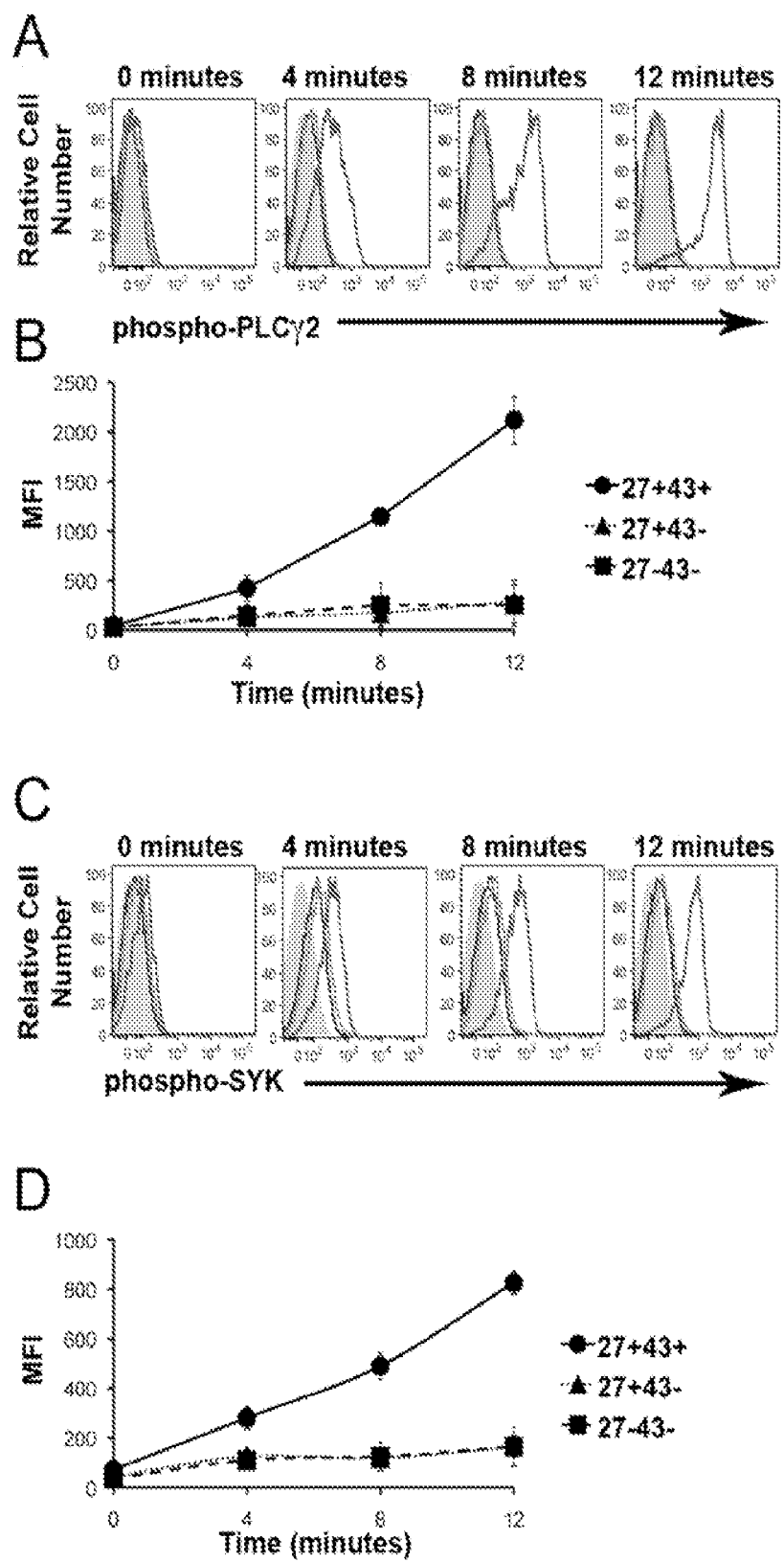
FIG. 6. Adult peripheral blood CD20+CD27+CD43+ B cells exhibit tonic intracellular signaling. A) Adult peripheral blood mononuclear cells were evaluated for phosphorylation of PLC-γ2 by intracellular staining after phosphatase inhibition. Cells were unexposed (0) or were exposed to pervanadate for 4, 8, and 12 minutes and then fixed, permeabilized and stained for surface antigens and pPLC-γ2 with specific immunofluorescent antibodies. Histograms show fluorescence produced by isotype control antibody (in solid gray) and by anti-pPLC-γ2 for CD20+CD27–CD43– (27–43–) cells (curve above gray area), for CD20+CD27+CD43– (27+43–) cells (curve above gray area), and for CD20+CD27+CD43+ (27+43+) cells (curve farthest to right). Because isotype control antibody staining by "fluorescence minus one" did not vary between the three cell populations under study, only a single control tracing is shown. Results for one of 3 comparable experiments is shown. B) Mean values of MFI are shown (with lines indicating standard errors of the means) for intracellular pPLC-γ2 staining at various time points from 3 separate adult peripheral blood samples. C) Adult blood mononuclear cells were evaluated for phosphorylation of Syk by intracellular staining after phosphatase inhibition. Cells were unexposed (0) or were exposed to pervanadate for 4, 8, and 12 minutes and then fixed, permeabilized and stained for surface antigens and pSyk with specific immunofluorescent antibodies. Histograms show fluorescence produced by isotype control antibody (in solid gray) and by anti-pSyk for CD20+CD27–CD43– cells (curve above or slightly to right of gray area), for CD20+CD27+CD43– cells (curve above or slightly to right of gray area), and for CD20+CD27+CD43+ cells (curve farthest to right). Results for one of 3 comparable experiments is shown. D) Mean values of MFI are shown (with lines indicating standard errors of the means) for intracellular pSyk staining at various time points from 3 separate adult peripheral blood samples.

To further evaluate IgM-secreting, T cell-stimulating adult peripheral blood B cells, tonic intracellular signaling was examined by phosphoflow analysis of phosphorylated PLC-γ2 and Syk, as described above. Untreated B cells showed little evidence of phospho-PLC-γ2 or phospho-Syk. As with cord blood B cells, within minutes of phosphatase inhibition it was found that CD20+CD27+CD43+ B cells expressed substantial levels of phospho-PLC-γ2 and phospho-Syk, whereas the levels of phospho-PLC-γ2 and phospho-Syk in CD20+CD27+CD43− and CD20+CD27−CD43− B cells changed little (FIG. 6). Thus, the small population of CD20+CD27+CD43+ adult blood B cells, and only that population, displays tonic intracellular signaling. In sum, because CD20+CD27+CD43+ adult blood B cells reproduce the characteristics of CD20+CD27+CD43+ cord blood B cells in manifesting 3 key B1 cell functional characteristics, CD27 and CD43 identify a B cell population throughout ontogeny that represents the human equivalent of murine B1 cells.

CD43 Expression is not Inducible on CD43− B Cells.

Figure 7:
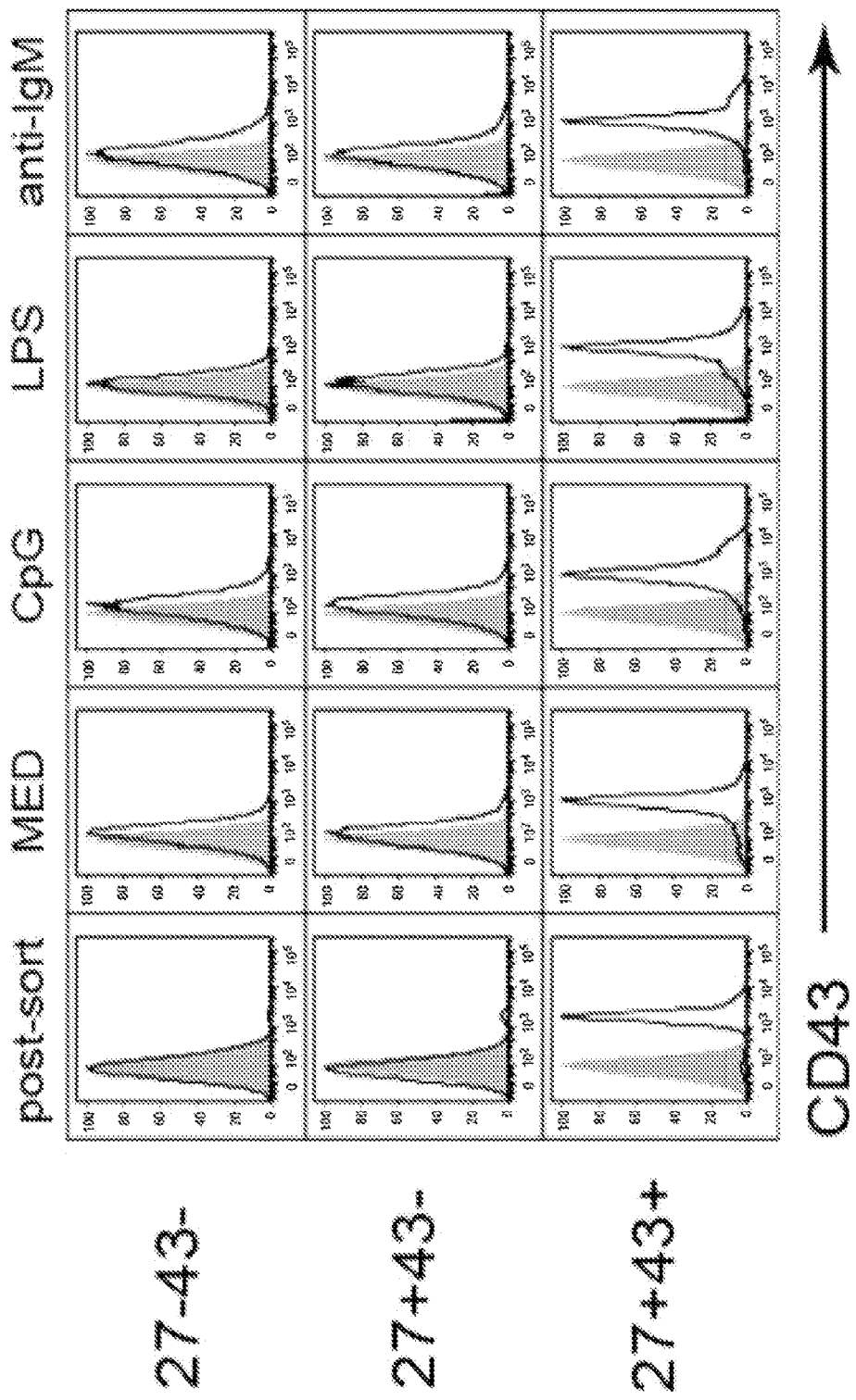
FIG. 7. CD43 expression is not inducible on CD43-B cells. Sort-purified CD20+CD27–CD43– (27–43–), CD20+CD27+CD43– (27+43–) and CD20+CD27+CD43+(27+43+) adult peripheral blood B cells were cultured in medium alone (MED), or were stimulated with either CpG (10 μg/ml), LPS (25 μg/ml) or anti-IgM (7 μg/ml) for 4 days after which CD43 expression was evaluated. Results are shown for one of 3 separate adult peripheral blood samples.

To rule out the possibility that CD43 is an inducible cell surface antigen, like CD5 (Cong et al., 1991; Freedman et al., 1989), CD20+CD43− adult peripheral B cells were cultured (both CD27+ and CD27−), and CD20+CD27+CD43+ adult B cells, with medium alone, or with either LPS, CpG, or anti-IgM for 4 days and re-assessed expression of CD43. It was found that CD43 expression was not induced on initially CD43− B cells after stimulation (FIG. 7). In addition, CD43 expression was not lost from initially CD43+ B cells. Thus, CD43 expression on B cells is not inducible by a number of different exogenous stimuli and represents a stable marker for this B cell population. In follow up experiments, it was found that under extreme conditions, CD43 can be induced on previously negative CD43 B cells. However, B1 cells are distinguishable, since these cells can express low levels of CD69, CD70 and CD80, which activated B cells expressing CD43 do not.

Enumeration of CD20+CD27+CD43+ B Cells in Normal Individuals.

Figure 8A:
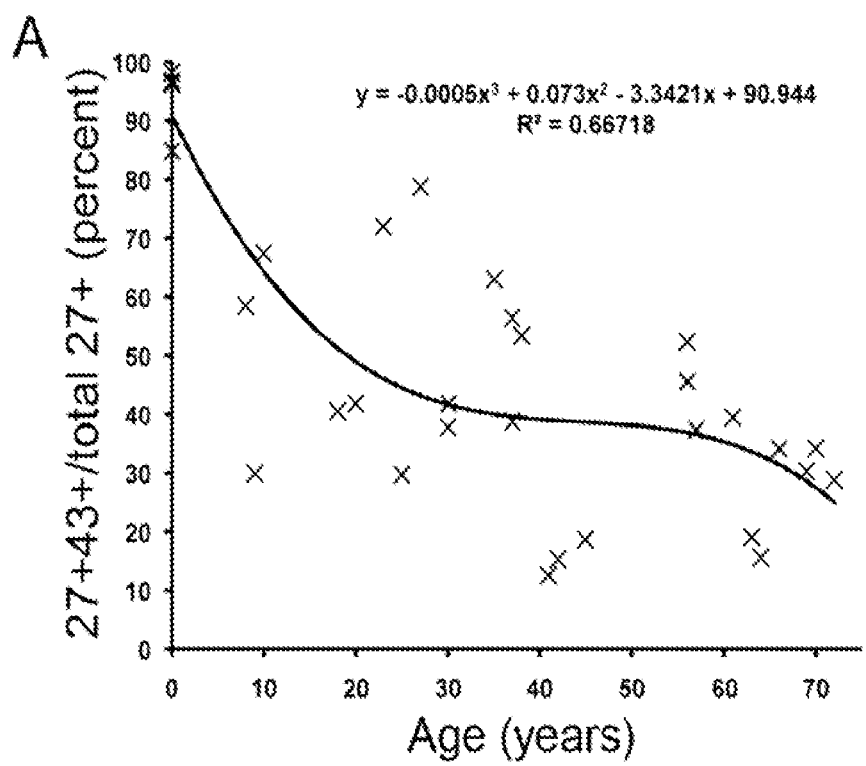
FIG. 8. The CD20+CD27+CD43+ B cell fraction decreases with age. A) Cord blood (n=6) and peripheral blood (n=34) samples were obtained and analyzed for the number of CD20+CD27+CD43+ cells expressed as a percent of the total number of CD20+CD27+ cells. The line through the datapoints represents a cubic regression curve fit. B) Mean values for the proportion of CD43+ B cells among CD20+CD27+ B cells are shown for two age groups of under age 20 and over age 50 (n=10 each), with lines indicating the standard errors of the means.
Figure 8B:
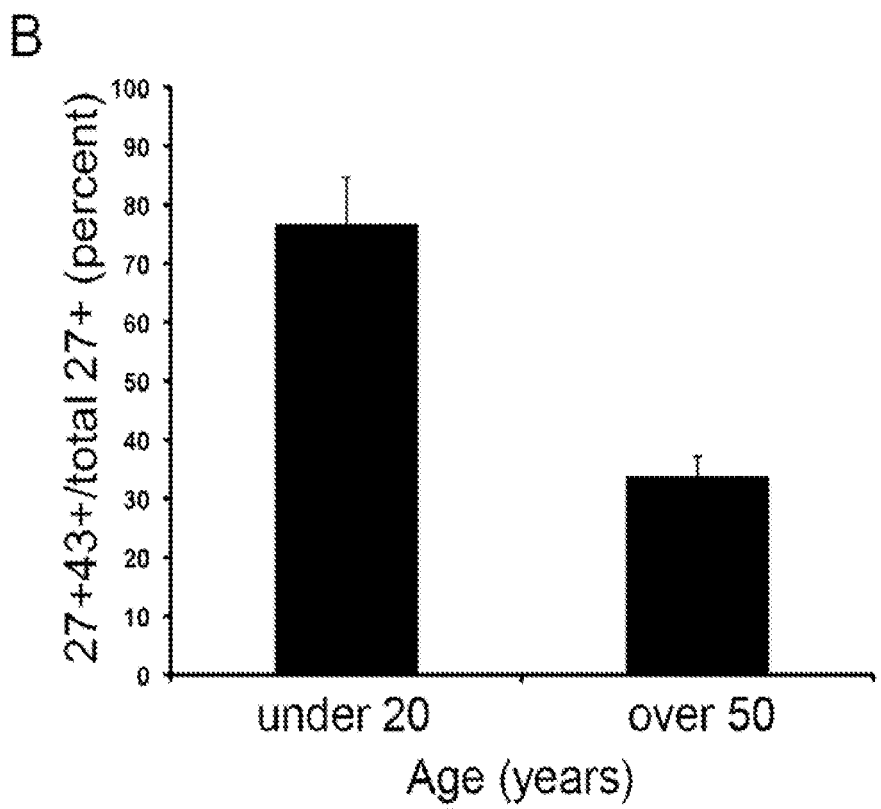

To evaluate the variation in B cell populations among normal individuals and with advancing age, 6 umbilical cord and 34 adult peripheral blood samples obtained from normal volunteers were screened. As expected, the fraction of B cells expressing CD27 that lack CD43 (CD20+CD27+CD43−) increased from very few in cord blood to more than 50% in the 6th through 8th decades as (true) memory B cells accumulated. Conversely, it was found that the fraction of CD27+ B cells expressing CD43 (CD20+CD27+CD43+) declined from nearly 100% in cord blood to fewer than 10%, on average, in the $6^{th}$ through $8^{th}$ decades (FIG. 8A). Various regression models were used to examine this trend; the cubic model had a higher R2 than the quadratic model and the line so generated is shown. The same data was separately evaluated by comparing samples from individuals under age 20 (n=10) with samples from individuals over age 50 (n=10) (FIG. 8B). This comparison shows a more than 2-fold difference in the proportion of CD43+ B cells among CD20+CD27+ B cells in these two age groups that is statistically significant by Student's t test.

Discussion I

The identity and even existence of human B1 cells has been in doubt for many years, because of the absence of known cell surface markers for this population. This contrasts with the murine system, in which the utility of CD5 to identify B1 cells has led to an accumulation of information concerning the unique developmental and behavioral characteristics of this B cell subset. Herein three foundational features elucidated through studies of murine B1 cells were applied to the human system by working in reverse to discover the surface antigens expressed on B cells that produce these index functional characteristics. By evaluating spontaneous IgM secretion, efficient T cell stimulation, and tonic intracellular signaling, in conjunction with somatic hypermutation, it was determined that human B1 cells are CD20+ B cells that co-express CD27 and CD43, in both umbilical cord blood and in adult peripheral blood. The results are very clear cut, in that not only do CD20+CD27+CD43+ cells express each of three key functional characteristics, but other B cell populations do not express even one. Overall, this represents a major step forward in the translation of what is known about B1 cell physiology and pathology from animal models to the human condition, and will provide the means to correctly determine the number and function of B1 cells in various disease states and in normal individuals at various stages of life.

It is important to note that the CD20+CD27+CD43+ cells identified as human B1 cells are not in any way related to differentiated follicular B cells that might secrete IgM, such as plasma cells or plasmablasts, because human B1 cells did not express CD138 (which is acquired by differentiated plasma cells, reference (Klein and Dalla-Favera, 2007)), because human B1 cells did express CD20 (which is lost during differentiation at the plasmablast stage, reference (J ego et al., 2001)), and because neither CD138 acquisition nor CD20 loss occurred following culture of human B1 cells with IL-6 for 5 days (data not shown). Further, CD43 is a durable and stable marker for the human B1 cell population inasmuch as it could not be induced on CD43-B cells as a result of stimulation by LPS, CpG, or anti-Ig and in this way differs from CD5 in the murine system which is an activation antigen for B2 cells (Cong et al., 1991; Freedman et al., 1989). Thus, there is no evidence that human CD20+CD27+CD43+ B1 cells are in transition from one developmental, activation or differentiation stage to another.

The phenotypic composition of B1 cells has already led to additional insights regarding human B cell populations. Firstly, whereas peripheral (cord) blood at birth would seem to be necessarily devoid of memory B cells, as has been previously reported (Agematsu et al., 1997; Maurer et al., 1990), our results indicate that a population of CD27+ B1 cells is, in fact, present, as has been suggested (Shi et al., 2005), furthering the notion that CD27 is not an immutable indicator of memory B cell status, as suggested by its presence on developing B cells (Nilsson et al., 2005). Secondly, whereas adult peripheral memory B cells have been reported to efficiently stimulate T cells (Good et al., 2009), our results indicate that this function is actually contributed by B1 cells contained within the CD27+ population and not by memory B cells per se. These latter results suggest that the features ascribed to memory B cells must now be re-evaluated, and that functional studies of CD27+ B cells should proceed only after depletion of CD27+CD43+ B1 cells to insure a more homogeneous memory B cell population.

The overlap and confusion between CD27+CD43+ B1 cells and CD27+ memory B cells may be particularly acute with respect to so-called "IgM memory" B cells. It has been reported that IgM memory B cells are responsible for controlling infections produced by *Streptococcus pneumoniae* and other encapsulated organisms (Kruetzmann et al., 2003); however, it seems likely that the population of IgM memory B cells studied in previous work may well have included B1 cells, suggesting that CD27+CD43+ B1 cells are responsible for producing anti-PC antibody in the human system as they are in the murine system.

The number of human CD27+CD43+ B1 cells found in the peripheral circulation was small, and this raises the possibility that human B1 cells may be primarily located in a reservoir other than the peripheral circulation. This is, in fact, the situation with mouse B1 cells, which are located primarily in coelomic cavities and the spleen. The report that anti-*Streptococcus pneumoniae* IgM memory B cells are generated in the spleen (Kruetzmann et al., 2003) is reminiscent of previous reports on mouse B1 cells indicating they also require the spleen for development (Wardemann et al., 2002), and again raises the possibility that at least some IgM memory B cells may actually be human B1 cells.

Regardless of the relationship between human B1 cells and IgM memory B cells, the number of CD27+ B cells declines with advancing age (Shi et al., 2005), and our results indicate that the fraction of CD43+ B1 cells within the CD27+ population declines even more precipitously. Thus it is likely that B1 cell protective natural antibody also declines with age, and this may explain, at least in part, the susceptibility of aged individuals to overwhelming infection by encapsulated organisms.

As noted earlier, CD5 is not a good marker for human B1 cells because it is known to be expressed by follicular B cells at various stages of development and activation. In preliminary experiments it was found that CD20+CD27+CD43+ may be either CD5+ or CD5−, and that these two subpopulations are equivalent in spontaneous IgM secretion, efficient T cell stimulation, and tonic intracellular signaling (data not shown). This further emphasizes the lack of information relative to B1 cells conveyed by CD5 expression in the human system.

It has been conjectured for many years that the normal counterpart for malignant CD5-expressing chronic lymphocytic leukemia cells lies in human B1 cells; however, the identity of such cells has not been known up until now. With the characteristics of human B1 cells in hand, a number of similarities between normal human B1 cells and malignant CLL cells, at least of the poor prognosis type, are evident. For example, both express CD20, CD27, and CD43; some normal B1 cells express CD5 as do malignant CLL cells; and, both express relatively non-mutated immunoglobulin (Damle et al., 1999; Hamblin et al., 1999; Jung et al., 2003). In addition, it was found that normal human B1 cells express ZAP-70 and ILT3 (unpublished observations) like CLL cells (Best et al., 2006; Colovai et al., 2007). Parenthetically, with respect to pathophysiology, the chronically activated phenotype of normal B1 cells may predispose to malignant transformation. Thus, in regards to CLL, in some respects we may be back to the future that was postulated 30 years ago, to wit, that the normal counterpart cell for CLL is the human B1 cell, only now the true identity of the normal counterpart is known. This will, in turn, provide the means to carry out informative experiments to elucidate the nature of CLL neoplasia by comparing malignant CLL cells with the proper corresponding non-transformed B cells.

In sum, a subset of human peripheral CD20+ B cells has been identified, specifically encompassing a small proportion that expresses CD27 and CD43 and is present in both umbilical cord and adult peripheral blood, recapitulates key functional characteristics of murine B1 cells and for this reason is here denoted as the human B1 cell population. Identification of this population carries important implications for the functions previously ascribed to memory B cells, for the origin of chronic lymphocytic leukemia, and for the role of human B1 cells in health and disease.

Experimental Details II

Introduction

A primary function of B lymphocytes is immunoglobulin production; however, the therapeutic benefit of B cell depletion in autoimmune diseases previously thought to be T cell-mediated suggests that some B cells fulfill other roles in autoimmunity. Hereinbelow, the human B1 cell population identified above was examined for T cell stimulatory activity. Two kinds of B1 cells were found that are distinguished by multiple surface markers and distinct transcriptomic profiles. In both umbilical cord and adult peripheral blood a CD11b− subset constitutes about 90% of B1 cells whereas a CD11b+ subset constitutes about 10% of B1 cells. Significantly, these B1 cell populations differ functionally. CD11b− B1 cells spontaneously secrete much more IgM than CD11b+ B1 cells. In contrast, CD11b+ B1 cells express more CD86, and more efficiently stimulate allogeneic CD4+ T cell expansion, than CD11b− B1 cells. The frequency of these CD11b+ B1 cells is markedly elevated in lupus patients. CD11b+ B1 cells in lupus patients express more CD86, and have increased T cell stimulating activity in disease. Thus, a novel T cell-interacting B1 cell population is disclosed whose abundance and activity reflects, and is a therapeutic target for, autoimmune disease.

Materials and Methods

Donors and Samples: Adult peripheral blood samples were obtained by venipuncture of adult volunteers after obtaining informed consent in accordance with the Declaration of Helsinki. Additional samples in the form of leukopacks were obtained from the New York Blood Center on the day of donation. These healthy controls were mean age 51, 78% female, 85% European, 13% Asian, and 2% Hispanic. Anonymous umbilical cord blood samples were obtained from the Tissue Donation Program at The Feinstein Institute for Medical Research. This study was approved by, and all samples were obtained in accordance with, the Institutional Review Board of the North Shore-LIJ Health System.

Processing: All blood samples were treated in a similar manner and processed promptly upon receipt. Mononuclear cells were obtained by density gradient separation using lymphocyte separation medium (Cellgro). Except as otherwise noted, mononuclear cells were then washed and resuspended in RPMI 1640 (Cellgro) containing 10% fetal calf serum plus 2 mM L-glutamine, 10 mM HEPES (pH 7.25), 100 U/ml penicillin and 100 μg/ml streptomycin.

B Cell Enrichment: For some experiments (FIGS. 9F, 10, 11G and 12E) B cells were enriched by CD19 positive selection using the EasySep Human CD19+ B cell magnetic bead selection kit (StemCell Technologies) according to the manufacturer's instructions. For some experiments (FIG. 14C) B cells were enriched by CD20 positive selection using the EasySep Human CD20+ B cell magnetic bead selection kit (StemCell Technologies).

Cell Sorting and Flow Cytometric Analysis: Enriched B cells and mononuclear cells were immunofluorescently stained and then sort-purified on an Influx instrument (BD Biosciences). Cells to be sorted were suspended in 2 mM EDTA in dye-free RPMI supplemented with 10% fetal calf serum at a concentration below 50 million cells per milliliter. Flow cytometric analysis of immunofluorescently stained cells was carried out on a BD Biosciences LSR-II instrument. Post-sort analysis showed less than 1% CD3 positivity for sort-purified CD19-enriched B cells and less than 3% CD3 positivity for sort-purified mononuclear (not pre-enriched) B cells.

ELISA: Immunoglobulin secretion was determined by ELISA assay, as previously described.

Allogeneic Stimulation: Naïve CD4+ T-cells were negatively selected from PBMC and co-cultured with sort-purified, irradiated B cells at a ratio of 2:1, as previously described. For the allogeneic stimulation assays shown in FIG. 11C, 11D, 50,000 B cells were seeded per well. For the allogeneic stimulation assays shown in FIG. 4E, comparing lupus patients to normal controls, 1,000 B cells were seeded per well to accommodate the smaller cell numbers that could be obtained from lupus patients. In some experiments B cells were exposed to neutralizing anti-CD86 antibody (10 μg/ml) for one hour prior to, and then during, co-culture. Cultures were pulsed with 0.75 microcuries [$^3$H]thymidine for the last 8 hours of 5 day cultures and counts per minute (cpm) determined by scintillation counting.

Microarray Analysis: RNA was isolated from sort-purified naïve B cells (CD20+CD27−CD43−), memory B cells (CD20+CD27+CD43−), CD11b+ B1 cells (CD20+CD27+CD43+ CD11b+), and CD11b− B1 cells (CD20+CD27+CD43+ CD11b−), from 3 normal individuals per subset, using the Qiagen RNeasy plus Minikit according to the manufacturer's instructions (Qiagen). RNA was analyzed for gene expression using the Illumina platform (Illumina, San Diego, Calif.). The human HT-12 v4 Expression BeadChip was used that interrogates >47,000 target probes for genes obtained from the National Center for Biotechnology Information Reference Sequence (NCBI) RefSeq Release 38 and other sources. Initial data analysis and quality control checks were performed using GenomeStudio software (Illumina). The data for all 12 samples was quantile normalized without background subtraction and exported as a project for additional analysis using Partek software (Partek® Genomic Suite v6.5). An ANOVA analysis was performed for all samples and heat-maps were generated for genes with differential expression between B1 cell subsets. Data is publically available with accession number GSE29717 at Gene Expression Omnibus.

Photomicroscopy: Sort-purified B cells were cytocentrifuged (Shandon), stained with Wright-Giemsa, and imaged at 40× (Zeiss Axiovert). CD11b+ B1 cells stained with Hoechst 33342 were single cell-sorted onto an Ampligrid (Beckman Coulter), excited by UV illumination, and imaged at 40× (Zeiss Axiovert). Sort-purified B cells for confocal imaging were fixed in paraformaldehyde, adhered to poly-lysine-coated slides, excited at 488, 568, and 647 nm, and imaged at 60× (Olympus Fluoview 300).

B1 Cell Stimulation: CD20+CD27+CD43+ CD11b− human B1 cells were sort-purified from adult peripheral blood and were cultured with PMA at 100 ng/ml plus ionomycin at 400 ng/ml (P+I), SAC at 0.005% plus IL-2 at 5 ng/ml (SAC+IL2), and anti-IgM at 7 μg/ml plus anti-CD40 at 10 μg/ml (αIgM+αCD40), in RPMI medium in round bottom wells.

Reagents: Fluorescently labeled antibodies (anti-CD5-PE-Cy7, anti-CD11b-percp, anti-CD11b-PE, anti-CD11c-PE, anti-CD14-PE, anti-CD20-V450, anti-CD20-APC-Cy7, anti-CD21-PE, V500-streptavidin, anti-CD23-PE, anti-CD27-V450, anti-CD27-APC, anti-CD43-FITC, anti-CD70-PE, anti-CD86-PE, anti-CD86-biotin, anti-CD69-percp, anti-CD70-PE, anti-CD71-PE, anti-CD80-PE, anti-IgD-PE, anti-IgM-PE) were obtained from BD Biosciences. Anti-CD11b-percp was obtained from abeam. Anti-CD14 Alexa647 was obtained from Biolegend. Anti-CD19 Alexa488 and Alexa568 streptavidin were obtained from Invitrogen. Anti-CD43-biotin was obtained from Thermo-Scientific. Anti-CD43-APC was obtained from eBioscience. Streptavidin was obtained from Biomeda. Anti-CD86 neutralizing antibody was obtained from eBioscience. Wright-Giemsa stain was obtained from Ricca chemical.

Results and Discussion

Figure 13A:
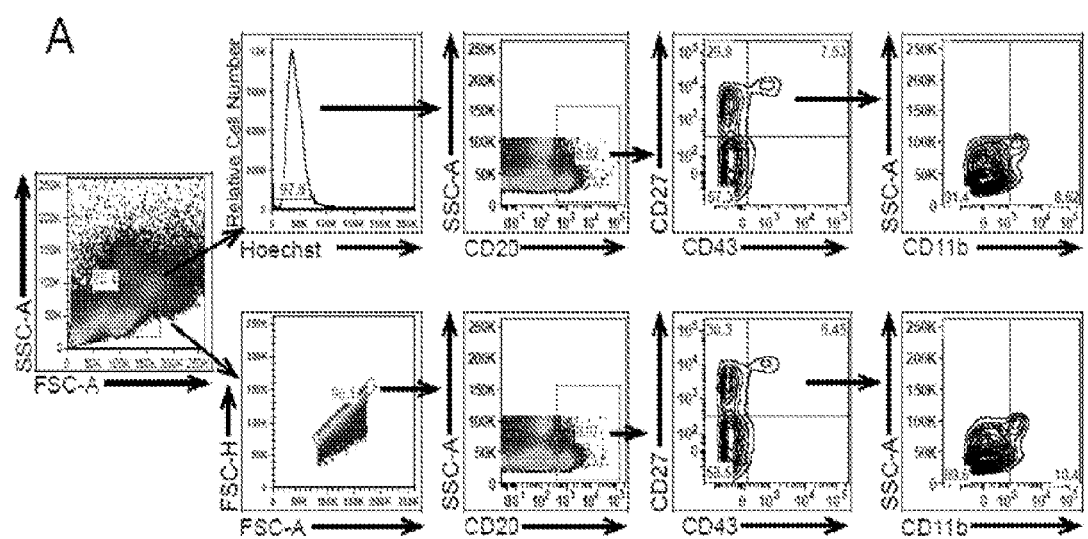
FIG. 13A-13B shows that CD11b+ B1 cells are readily identified after doublet exclusion, and that sort purified CD11b+ and CD11b− B1 cells are singlets whose phenotype does not change with in vitro culture. (A) Adult peripheral blood mononuclear cells were stained with Hoechst 33342 and with fluorescent antibodies that recognize CD20, CD27, CD43, and CD11b, and were then evaluated by flow cytometric analysis. In the top row cells with single Hoechst-stained nuclei were analyzed. In the bottom row singlet cells discriminated by strict FSC-H/FSC-A gating were analyzed. Representative results from one of 3 comparable experiments are shown. (B) Sort-purified, Hoechst 33342-stained CD11b+ and CD11b− B1 cells were analyzed post-sort for doublet contamination by FSC-H/FSC-A discrimination and by assessment of single Hoechst-stained nuclei. Sort-purified B1 cells were analyzed post-sort for purity of CD11b+ and CD11b− populations and again after culture for 36 hours. Representative results from one of 3 comparable experiments are shown.

Human B1 cells obtained from both umbilical cord and adult peripheral blood express index functional features not expressed by other mature B cells and phenotype as CD20+ CD27+CD43+CD70− as discussed hereinabove. It is disclosed herein that these B1 cells can be sharply divided into two distinct populations by phenotypic criteria. Immunofluorescent staining reveals that some CD20+CD27+CD43+ B1 cells express CD11b whereas the bulk of B1 cells do not (FIG. 9A, 9B). Over a number of samples it was found that CD11b+ B1 cells represent 11.9%+/−1.1 (mean+/−SEM, n=67) of adult peripheral blood B1 cells and 13.2%+/−3.4 (n=6) of umbilical cord blood B1 cells; CD11b− B1 cells represent 88.1%+/−1.2, of all adult peripheral blood B1 cells and 86.8%+/−3.4 of umbilical cord blood B1 cells (FIG. 9C, 9D). In view of evidence in the murine system that B1 cells readily form aggregates (Ghosn et al., 2008), and the association of CD11b with the monocyte lineage, it was verified that CD11b expression is an intrinsic property of some human B1 cells. DNA was stained with Hoechst 33342 and then analyzed only those cells that were singlets (FIG. 13A); with this approach it was established that among cells defined on the basis of having only one nucleus, some co-expressed CD20, CD27, CD43 and CD11b. Separately, strict FSC-H was exerted by FSC-A doublet gating (FIG. 13A), but regardless of the level of restriction, CD11b+ B1 cells were readily identified in similar proportions within the B1 population.

Figure 9E:
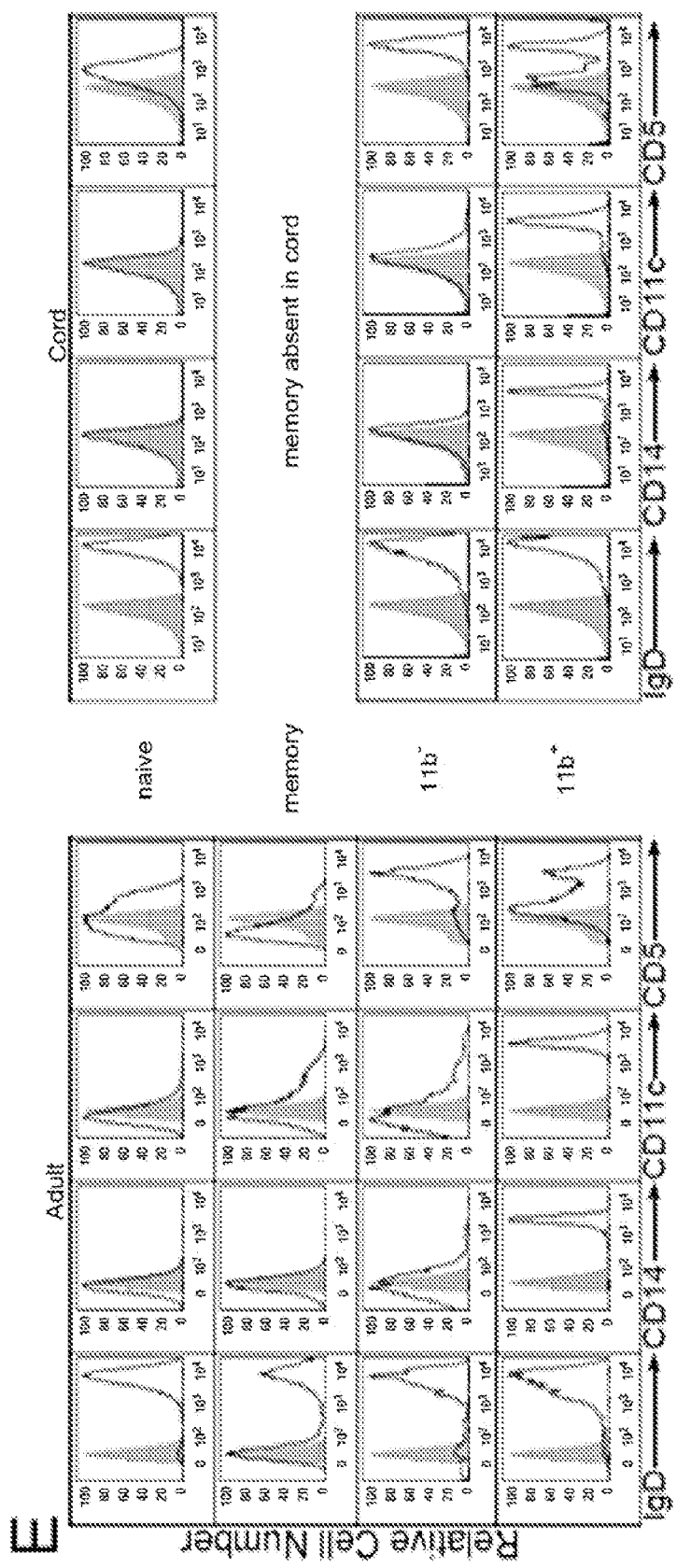
FIG. 9A-9D. CD11b expression divides human B1 cells into two phenotypically distinct subsets. (A-D) Adult peripheral blood and umbilical cord blood mononuclear cells were immunofluorescently stained for CD20, CD27, CD43, and CD11b, and were then evaluated by flow cytometric analysis. (A) The gating strategy used to separate CD20+CD27+ CD43+ B1 cells into CD11b− and CD11b− populations for a representative adult blood sample. (B) Expression of CD11b on gated CD20+CD27+CD43+ B1 cells (solid line) along with isotype control (solid gray) for a representative adult blood sample. The percent of CD20+CD27+CD43+ B1 cells that are CD11b− and CD11b+ is shown for adult peripheral blood samples (C) (n=67) and umbilical cord blood samples (D) (n=6) as mean plus standard errors of the means. (E) Adult peripheral blood and umbilical cord blood mononuclear cells were stained for IgD, CD14, CD11c and CD5 in addition to CD20, CD27, CD43 and CD11b, and then evaluated by flow cytometric analysis. Expression of IgD, CD14, CD11c, and CD5 by naïve (CD20+CD27−CD43−) and memory (CD20+CD27+CD43−) B cells and by CD11b− and CD11b+ B1 (CD20+CD27+CD43+) cells is shown for representative adult and cord blood samples (one of 3 each) with isotype control in solid gray. (F) Adult peripheral blood was obtained from 3 individuals. RNA was prepared from sort-purified populations of naïve, and memory B cells, and CD11b− and CD11b+ B1 cells and analyzed for gene expression by microarray. Expression levels for CD11b, CD14 and CD11c transcripts are shown in the form of a heat map. (G) Adult peripheral blood mononuclear cells were stained for CD20, CD27, CD43, CD11b, and CD80 and were then evaluated by flow cytometric analysis. CD80 expression by naïve (CD20+CD27−CD43−) and memory (CD20+CD27+ CD43−) B cells, and by CD11b+ and CD11b− B1 (CD20+ CD27+CD43+) cells, is shown as colored lines, along with isotype control (solid gray).
Figures 9F, 9G:
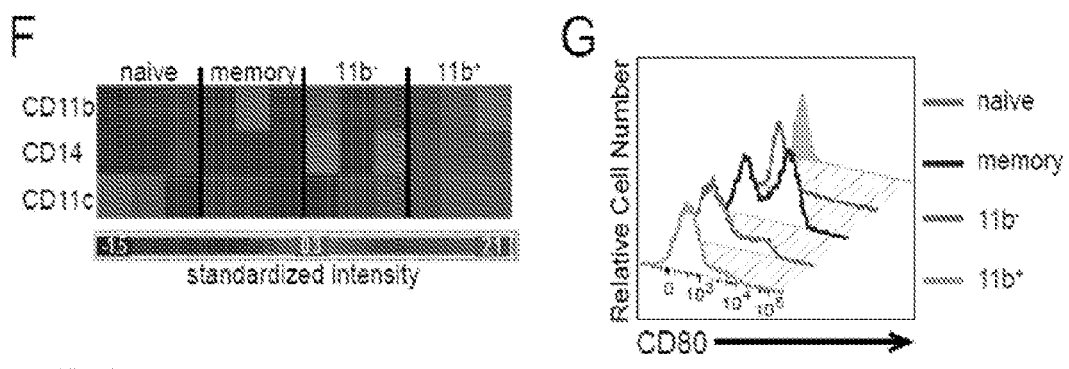

Several phenotypic differences distinguish CD11b+ and CD11b− B1 cells. Notably, CD11b+ B1 cells express CD14 and CD11c, whereas other B cell types (CD11b− B1 cells, memory B cells, and naïve B cells) do not (FIG. 9E). The distinctive staining for CD11b, CD14 and CD11c is mirrored in the unique expression of CD11b, CD14 and CD11c transcripts (FIG. 9F).

Despite unique surface marker and gene expression, CD11b+ B1 cells are similar to CD11b− B1 cells (and naïve B cells) in being predominantly IgD+, whereas a majority of memory B cells are IgD negative. Surface immunoglobulin expression marks CD11b+ and CD11b− B1 cells as B cells. It is highly unlikely that binding of anti-IgD, or antibodies binding other defining determinants, is non-specific inasmuch as additional antibodies bound poorly (anti-CD80) to CD11b+ or CD11b− B1 cells despite binding to memory B cells (FIG. 9G), or not at all (anti-CD71) despite binding CD11b+CD20-CD71+ cells (data not shown).

Unlike CD11b− B1 cells that are mostly CD5+, the majority of CD11b+ B1 cells either do not express CD5 or express very low levels of CD5 (FIG. 9E). These results further show that identification by CD5 expression not only omits approximately ¼ of all B1 cells, but preferentially omits in particular one of two B1 cell subpopulations.

Figure 10:
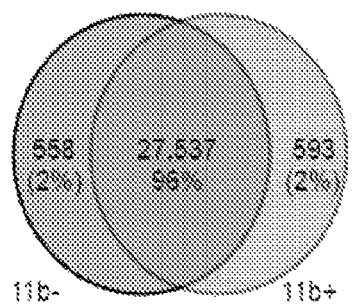
FIG. 10. CD11b expression divides human B1 cells into two transcriptionally distinct subsets. Gene expression microarray analysis was performed on RNA that was isolated from sort-purified naïve B cells (CD20+CD27−CD43−), memory B cells (CD20+CD27+CD43−), CD11b+ B1 cells (CD20+CD27+CD43+CD11b+), and CD11b− B1 cells (CD20+CD27+CD43+CD11b−) obtained from 3 normal individuals per B cell population. The expression of coding transcripts with well-established annotation (28,688) by CD11b+ and CD11b− B1 cells is shown in the form of a Venn diagram. Transcripts differentially expressed 2-fold greater by CD11b+ B1 cells are shown in lightest gray, transcripts differentially expressed 2-fold greater by CD11b− B1 cells are shown on the left hand side portion, and transcripts expressed similarly by CD11b− and CD11b+ B1 cells are represented by the dark orange overlap.

In sum, elevated expression of CD11b, CD11c, and CD14 constitutes a constellation of markers that defines a small subpopulation of B1 cells that is operationally CD11b+. Further evidence that CD11b+ and CD11b− B1 cells represent distinct groups is provided by the 1151 genes differentially expressed between these two populations (FIG. 10).

Figure 13B:
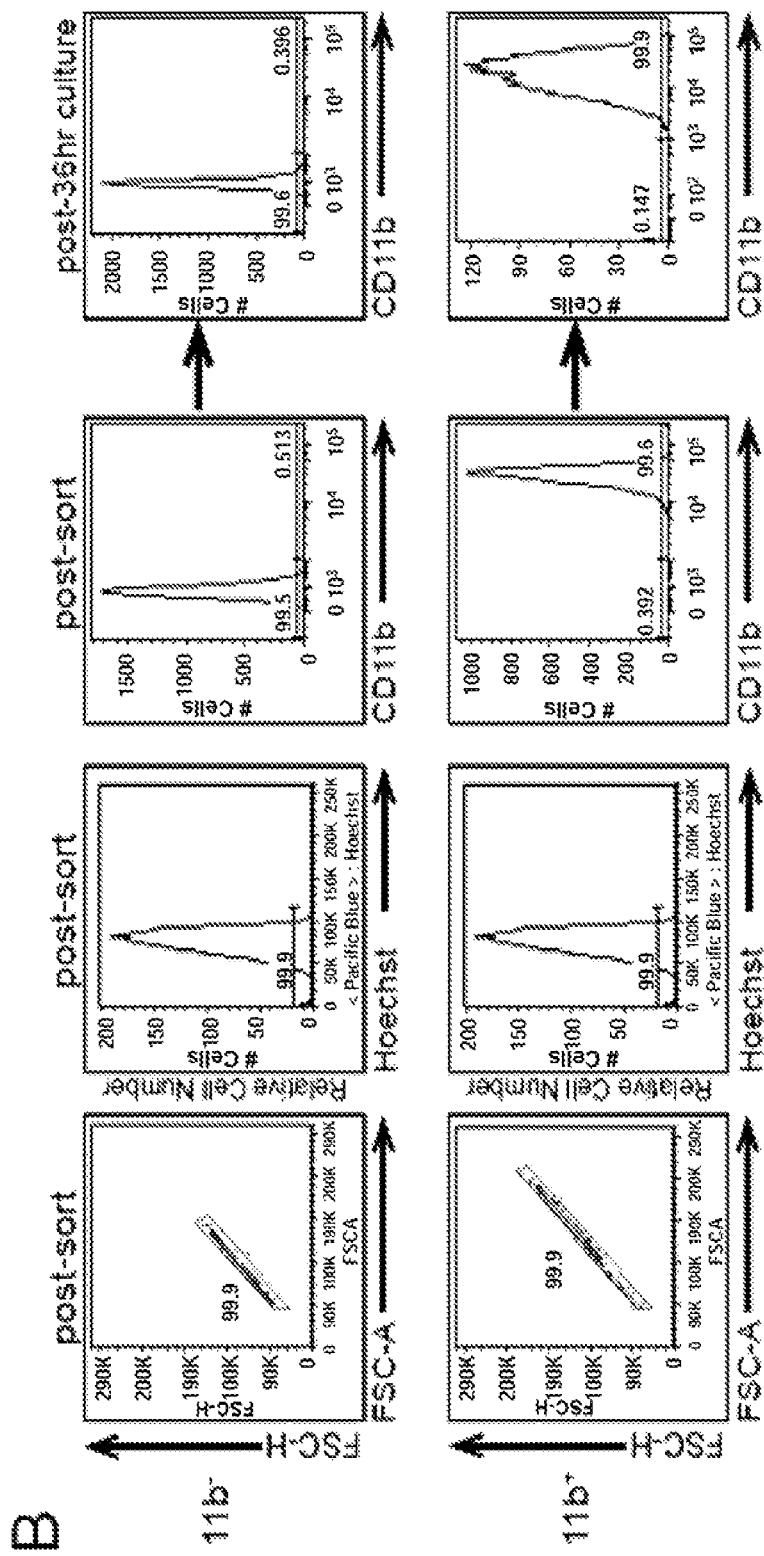
Figures 14A, 14B, 14C:
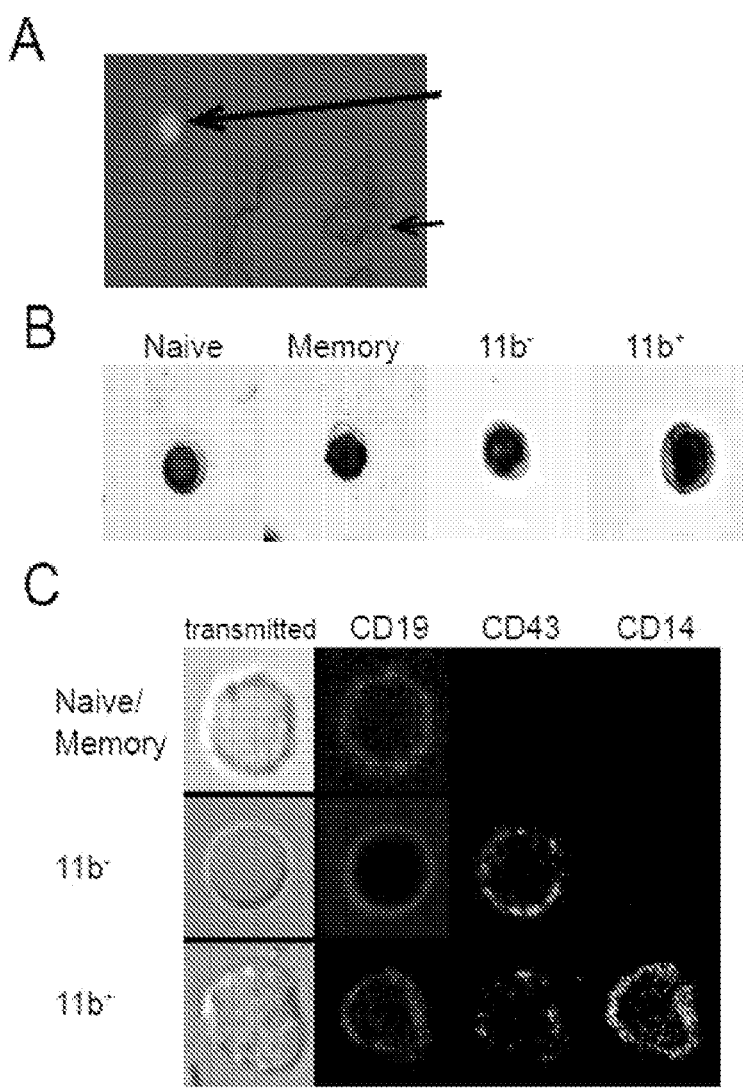
FIG. 14 shows that by direct visualization, CD11b+ B1 cells are singlets after sort-purification; CD11b+ B1 cells display typical lymphocyte morphology similar to other B cell populations; and, single CD11b+ B1 cells express CD19, CD43 and CD14 by confocal microscopy.

Further characterization of CD11b+ and CD11b− B1 cells was performed by examining isolated populations purified by cell sorting as described in Methods. To avoid potential doublets, $Ca^{++}$ was depleted with 2 mM EDTA, cell suspensions were agitated frequently, and strict doublet discrimination was utilized as discussed above. It was shown that sort-purified CD11b+ and CD11b− B1 cells were single cells without evidence of doublets by post-sort analysis on the basis of nuclear staining with Hoechst 33342 and FSC-H by FSC-A discrimination (FIG. 13B). In addition, Hoechst-stained cells were sorted in single droplets onto glass slides and showed the presence of only a single nucleus per event by direct visualization with fluorescence microscopy (FIG. 14A). Further, sort-purified B1 cells, both CD11b+ and CD11b−, were greater than 95% viable by propidium iodide staining.

CD11b+ and CD11b− B1 cells were examined by direct visualization after sort-purification. These B1 cells display typical round lymphocyte morphology without dendritic projections or multilobulated nuclei, as seen in Wright-Giemsa-stained and transmitted light images, much like other B cells (FIG. 14B). Moreover, sorted single CD11b+ B1 cells co-expressed CD19, CD43 and CD14, as determined by confocal microscopy (FIG. 14C). In addition, and as expected, nominally CD11b− B1 cells were positive for CD19 and CD43 but failed to express CD14 (FIG. 14C). In contrast, naïve and memory B cells, though positive for CD19, did not express either CD43 or CD14 (FIG. 14C). Notably, there was no change in expression of CD11b when sort-purified CD11b+ and CD11b− B1 cells were separately cultured, with CD11b expression remaining high on CD11b+ B1 cells and remaining low on CD11b− B1 cells, suggesting that these populations are stable and not in the process of transitioning one to another (FIG. 13C). Moreover, stimulation of sorted CD11b− B1 cells with PMA plus ionomycin, SAC plus IL-2, or anti-Ig plus anti-CD40, failed to induce surface expression of CD11b (or CD14) despite upregulation of CD69 (data not shown), indicating that CD11b+ B1 cells are not simply an activated version of CD11b− B1 cells.

Sort-purified CD11b+ and CD11b− B1 cells were evaluated for two key features by which human B1 cells were originally defined—spontaneous IgM secretion and efficient T-cell stimulation—in order to assess functional distinctions that might differentiate these subsets. These two B1 cell populations were first tested for spontaneous secretion of immunoglobulin. CD11b+ and CD11b− B1 cells were cultured, as well as naïve (CD20+CD27−CD43−) B cells, from both adult and cord blood, and memory (CD20+CD27+CD43−) B cells from adult blood, without stimulation, for 5 days and assayed supernatants for IgM by ELISA. It was found that CD11b− B cells secreted much more IgM (19.4-fold higher, n=6 in adult blood; 10.3-fold higher, n=4 in cord blood) than CD11b+ B1 cells (FIG. 11A, 11B), whereas CD11b+ B1 cells still secreted more IgM than non-B1 B cells. Thus, CD11b− B1 cells are specialized for spontaneous secretion of IgM.

These two B1 cell populations were then tested for antigen presentation and T cell stimulation. Irradiated, sort-purified CD11b+ and CD11b− B1 cells were cultured, as well as irradiated naïve B cells, from adult and cord blood, and irradiated memory B cells from adult blood, with allogeneically mismatched CD4+ T cells for 5 days and evaluated DNA replication by measuring tritiated thymidine incorporation. CD11b+ B1 cells were found to stimulate T cell proliferation to a much greater extent (4.1-fold higher, n=4 in adult blood; 3.4-fold higher, n=3 in cord blood) than CD11b− B1 cells (FIG. 11C,11D), while CD11b− B1 cells in turn stimulated T cell proliferation to a greater extent than non-B1 B cells.

Figures 11A, 11B, 11C, 11D, 11E, 11F, 11G, 11H:
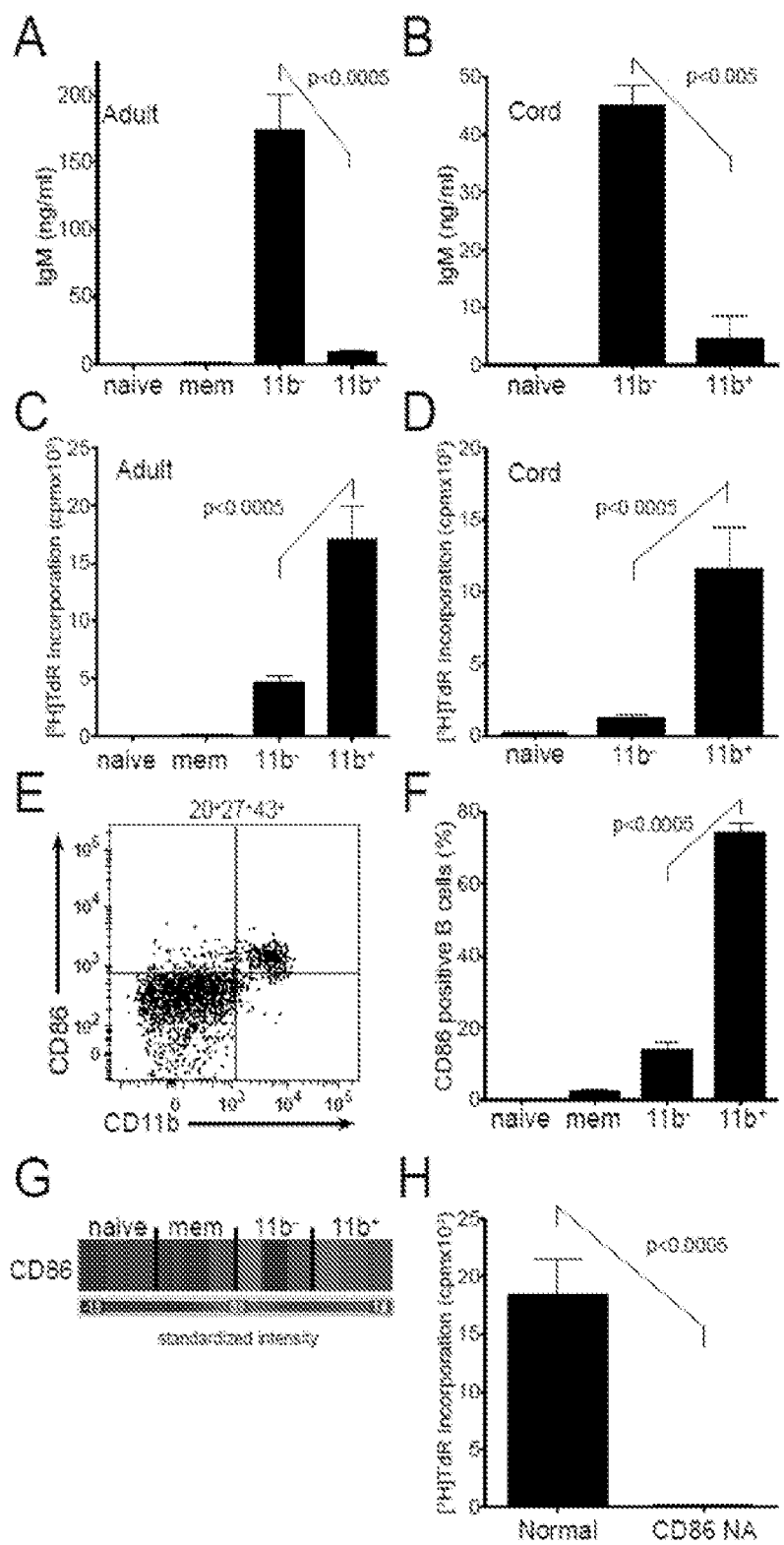
FIG. 11A-11H. CD11b expression divides human B1 cells into two functionally distinct subsets. Sort-purified CD20+ CD27−CD43− (naïve) B cells, CD20+CD27+CD43+ CD11b− (11b−) and CD20+CD27+CD43+CD11b+(11b+) B1 cells were obtained from adult peripheral blood and umbilical cord blood samples, and sort-purified CD20+ CD27+CD43− memory (mem) B cells were obtained from adult blood. (A,B) B cells were cultured at 1×10⁶ cells per ml for 5 d, after which supernatants were evaluated for secreted IgM by ELISA. Mean values are shown along with lines indicating SEM for 6 adult blood samples (A) and 4 cord blood samples (B) for each population. (C,D) B cells were irradiated and co-cultured 1:2 with negatively selected allogeneic CD4+ T cells for 5 d after which proliferation was measured by incorporation of tritiated thymidine during the last 8 hours of triplicate cultures. Mean cpm values are shown along with lines indicating SEM for 4 adult blood samples (C) and 3 cord blood samples (D) for each population. (E,F) Mononuclear cells from adult peripheral blood were immunofluorescently stained for CD20, CD27, CD43, CD11b and CD86 and were then evaluated by flow cytometric analysis. (E) Levels of CD86 and CD11b expressed by gated CD20+ CD27+CD43+ B1 cells in a representative adult peripheral blood sample. (F) Mean values for the proportion of CD86+ cells among CD20+CD27−CD43− (naïve) and CD20+ CD27+CD43− memory (mem) B cells, and among CD20+ CD27+CD43+CD11b− (11b−), CD20+CD27+CD43+ CD11b+(11b+) B1 cells, are shown with lines indicating SEM for 15 adult blood samples. (G) RNA was prepared from naïve B, memory B (mem), CD11b− B1 (11b−), and CD11b+ B1 (11b+) cells from 3 individuals and analyzed for gene expression by microarray as described in the legend to FIG. 10. Expression of CD86 transcripts is shown for each population in the form of a heat map. (H) Sort-purified and irradiated CD20+CD27+CD43+CD11b+ B1 cells were co-cultured with allogeneic CD4+ T cells as in 3C, above, with (CD86NA) or without (normal) anti-CD86 neutralizing antibody (CD86 NA). For anti-CD86-treated cultures, B1 cells were exposed to antibody for one hour prior to addition of T cells. Mean cpm values are shown along with lines indicating SEM for 3 adult peripheral blood samples analyzed in sextuplicate.

T cell stimulation by murine B1a cells has been reported to be attributable to CD86 expression (Zhong et al., 2007). Here it was found that among human adult peripheral blood B1 cells, expression of CD11b correlated with expression of CD86 (FIG. 11E), and that a much higher percentage of CD11b+ B1 cells expressed CD86 above isotype control values than did CD11b− B1 cells or naïve or memory B cells (FIG. 11F). This increased level of CD86 was mirrored by a much higher level of CD86 transcripts in CD11b+ B1 cells (FIG. 11G). Importantly, T cell stimulation induced by CD11b+ B1 cells was markedly reduced by anti-CD86 neutralizing antibody (FIG. 11H). Thus, CD11b+ B1 cells are specialized for efficient stimulation of T cells across an allogeneic barrier due, at least in part, to elevated expression of CD86.

The present results indicate that segregation of B1 cells according to CD11b expression is accompanied by functional polarization reflected in two foundational features: one population, which expresses CD11b and is the smaller of the two, strongly stimulates T cells through CD86 but produces modest levels of secreted antibody; and, a second population, that is CD11b− and is the larger of the two, secretes abundant amounts of IgM but is less effective in stimulating T cells. Taken together these findings indicate a unique division of labor between two subpopulations of human B1 cells, one of which is specialized for secretion of IgM, the other of which is specialized for interaction with T cells.

Figures 12A, 12B, 12C, 12D, 12E:
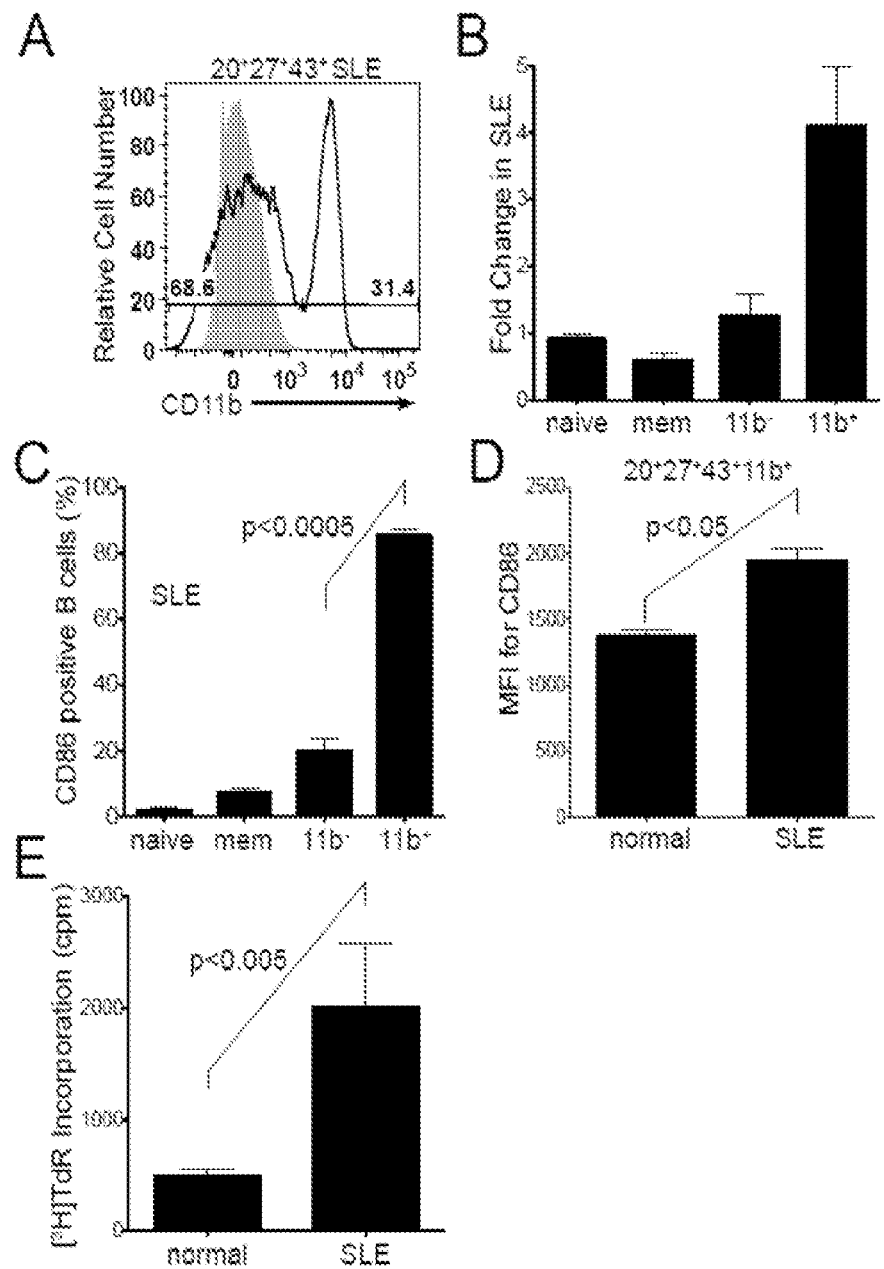
FIG. 12A-12E. CD11b+ human B1 cells are increased and functionally altered in patients with systemic lupus erythematosis. (A) Adult peripheral blood mononuclear cells from patients with SLE were immunofluorescently stained for CD20, CD27, CD43, and CD11b, and were then evaluated by flow cytometric analysis. Expression of CD11b on gated CD20+CD27+CD43+ B1 cells from a representative SLE patient (black line) with isotype control in solid gray. (B) Adult peripheral blood mononuclear cells from patients with SLE and from normal individuals were immunofluorescently stained for CD20, CD27, CD43, and CD11b, and were then evaluated by flow cytometric analysis. The percentages of CD20+CD27−CD43− (naïve) and CD20+CD27+CD43− memory (mem) B cells, and CD20+CD27+CD43+CD11b− (11b−) and CD20+CD27+CD43+CD11b+(11b+) B1 cells, among all B cells in SLE patients (n=15) were compared to the percentages of these populations among all B cells in normal controls (n=67). Ratios between these values are expressed as fold changes for B cell populations in SLE patients vs normal controls along with lines indicating SEM. (C,D) Adult peripheral blood mononuclear cells from 15 lupus patients were immunofluorescently stained for CD20, CD27, CD43, CD11b and CD86 and were then evaluated by flow cytometric analysis. (C) Mean values for the proportion of CD86+ cells among CD20+CD27−CD43− (naïve) and CD20+CD27+CD43− memory (mem) B cells, and among CD20+CD27+CD43+CD11b− (11b−), and CD20+CD27+ CD43+CD11b+ (11b+) B1 cells are shown with lines indicating SEM. (D) CD86 mean fluorescence intensity (MFI) on CD11b+ B1 cells from 15 normal control (normal) and 15 lupus patient (SLE) adult peripheral blood samples. Mean values are displayed along with lines indicating SEM. (E) Sort-purified and irradiated CD20+CD27+CD43+CD11b+ B1 cells from 3 normal control (normal) and 3 lupus patient (SLE) peripheral blood samples were cultured 1:2 in triplicate with negatively selected allogeneic CD4+ B cells for 5 d after which proliferation was measured by incorporation of tritiated thymidine. Mean cpm values are shown along with lines indicating SEM.

Induction of T cell proliferation across an allogeneic barrier is a surrogate for antigen presentation and in this sense the combination of elevated CD86 expression and efficient T cell stimulation on the part of CD11b+B1 cells may speak to a role in the generation of T cell abnormalities in autoimmune disease. To address this possibility, circulating B cells were phenotyped in 15 patients with lupus and 67 normal controls. In lupus patients, as in normal controls, CD20+CD27+CD43+ B1 cells lacked CD70 expression and thus were readily recognizable as true B1 cells. It was found that CD11b+ B1 cells underwent dramatic changes in lupus. Overall a large, greater than 4-fold increase in CD11b+ B1 cells was found (and only minimal changes in naïve, memory and CD11b− B1 cells). As a proportion of total B cells in nonnal controls and lupus patients, respectively: naïve cells were 66.0+/−1.6 versus 60.2+/−5.1; memory cells were 19.7+/−1.3 versus 11.7+/−2.1; CD11b− B1 cells were 11.4+/−1.0 versus 16.1+/−3.9; and CD11b+ B1 cells were 1.3+/−0.1 versus 5.3+/−1.1 (FIG. 12A, 12B). Both lupus patients and control subjects were mostly female and predominantly of either European or Asian descent, and mean ages were 36 and 51 years, respectively. Moreover, differences in B cell composition were similar when lupus samples were compared with samples from 15 of the 67 controls that were intentionally age- and gender-matched (whose B cells consisted of 66.4%+/−2.6 naïve, 21.1%+/−2.2 memory, 9.1%+/−1.5 CD11b− B1 and 0.7%+/−0.1 CD11b+ B1 cells). Not only is the proportion of CD11b+ B1 cells increased in lupus, but CD11b+ B1 cell expression of CD86 is increased as well. In lupus patients, as in normal controls, the frequency of CD86 expression by CD11b+ B1 cells far outweighed that of other B cell populations (FIG. 4C) and at the same time the amount of CD86 on CD86 on CD11b+ B1 cells, quantified by mean fluorescence intensity, was much greater in samples from lupus patients as compared to normal controls (FIG. 12D). Further, B1 cell function is altered in lupus. It was found that lupus CD11b+ B1 cells were more effective than normal CD11b+ B1 cells in stimulating T cells (FIG. 12E). Thus, in combination with the marked increase in CD11b+ B1 cells associated with lupus, the increased efficiency of T cell stimulation, identified in vitro, would have the effect of markedly enhancing T cell activation and effector function in vivo. Because many of the lupus samples were obtained from patients with inactive disease, increases in CD11b+ B1 cell numbers, CD86 expression, and T cell stimulation could not be correlated with clinical flares; however, the consistency of lupus associated B1 cell abnormalities may suggest a fundamental disorder that drives disease regardless of its periodic inflammatory intensity which may in turn relate to other factors.

Recognition of CD1 b+ B1 cells as a new B cell type with distinct characteristics provides a potential explanation for several prior observations regarding B cells in lupus. The increase in CD11b+ B1 cells, which express much higher levels of CD86 than other B cell populations, is consistent with the previous report that CD86+ B cells are increased in lupus (Bijl et al., 2001). Further, the increase in CD11b+ B1 cells, which like memory B cells express CD27, could well be responsible for the reported lupus-associated increase in CD27+ B cells (Jacobi et al., 2008), particularly in view of our results indicating a decline in true memory B cells (CD27+ B cells absent CD27+CD43+ B1 cells) in patient samples (FIG. 12B).

The previous work identifying CD27/CD43 co-expressing B cells as B1 cells emphasizes the peril in designating particular phenotypic determinants as negative criteria—had CD43-expressing cells been discarded, B1 cells would have been omitted from consideration along with myeloid cells. The current work indicating important divisions within the human B1 cell population on the basis of CD11b expression, leading to the identification of CD11b+ B1 cells, is again propelled by expression of surface determinants not classically associated with B cell status.

Notably, CD11b+ B1 cells are not the same as tissue-based FcRH4+ memory B cells because those B cells are predominantly negative for IgD and CD27 (Ehrhardt et al., 2005), whereas circulating CD11b+ B1 cells are positive for IgD and CD27. CD11b+ B1 cells are not the same as circulating CD21lo B cells identified in CVID patients because those B cells express low levels of CD21 and CD27, and no CD23 (Rakhmanov et al., 2009), whereas circulating B1 cells are strongly CD21 and CD27 positive and express CD23 (data not shown). CD11b+ B1 cells are not the same as circulating MZ B cells because those B cells express low levels of IgD and do not express CD23 (Weller et al., 2004) whereas circulating B1 cells express substantial levels of both. Thus, CD11b+ B1 cells constitute a distinct and unique human B cell population without known antecedent or parallel among human B cells.

Lupus autoimmune disease appears to result from a complex state of immune system dysfunction to which B cells contribute through their influence on T cells, among other mechanisms (Jacob and Stohl, 2010; Perosa et al., 2010; Sanz and Lee, 2010). In addition to earlier work in murine models suggesting the importance of B cells in the pathogenesis of lupus (Reininger et al., 1996), the recent success of anti-CD20 therapy has further emphasized the role of B cells in initiating and/or perpetuating autoimmune dyscrasias (Lund and Randall, 2010). The impact of B cell depletion on T cell abnormalities has demonstrated that there is a relevant effect of B cells on T cell stimulation in the context of autoimmune disease (Eming et al., 2008; Liossis and Sfikakis, 2008; Stasi et al., 2007). T cell-stimulating function is just the activity that shown to be concentrated within the very small CD11b+ B1 cell population, which expands greatly in lupus, upregulates CD86 expression, and becomes more immunostimulatory. These characteristics mirror previous findings in several murine models of lupus, in which it has been shown that B1 cell numbers are increased and antigen presentation is enhanced (Duan and Morel, 2006; Mohan et al., 1998; Xu et al., 2004), suggesting a pathogenic mechanism in which B1 cells present self-antigens to autoreactive T cells. Although it might be thought that the low frequency of CD11b+ B1 cells would be insufficient to substantially contribute to or alter immune activity, large effects from small populations are well known in the immune system, such as the generation of natural IgM from murine splenic B1 cells, the influence of human Treg cells on lupus disease, and the protection from pathogens afforded by myeloid dendritic cells (Barreto et al., 2009; Hambleton et al., 2011; Holodick et al., 2010; Kassianos et al., 2010). Moreover, the full size of the human B1 cell population could well be larger than suggested by its circulating component if one or more tissue reservoirs exist, as is the case with the preponderance of murine B1 cells within the peritoneal cavity.

Thus, the results demonstrate that subdivision of human B1 cells into CD11b+ and CD11b− populations is relevant not only for localizing activities that shape T cell function, but for autoimmune disease pathogenesis and pathopersistence as well. Identification of CD11b+ B1 cells as a new B cell type provides an important foundation for understanding how B cells influence the immune response in both health and illness, and shows a novel target for selective therapy in autoimmune disease that can unexpectedly leave the bulk of B cell responses intact.

LIST OF CITED REFERENCES

Agematsu, K., H. Nagumo, F. C. Yang, T. Nakazawa, K. Fukushima, S. Ito, K. Sugita, T. Mori, T. Kobata, C. Morimoto, and A. Komiyama. 1997. B cell subpopulations separated by CD27 and crucial collaboration of CD27+ B cells and helper T cells in immunoglobulin production. *Eur J Immunol.* 27:2073-9.

Agematsu, K., S. Hokibara, H. Nagumo, and A. Komiyama. 2000. CD27: a memory B-cell marker. *Immunol Today.* 21:204-6.

Barreto, M., R. C. Ferreira, L. Lourenco, M. F. Moraes-Fontes, E. Santos, M. Alves, C. Carvalho, B. Martins, R. Andreia, J. F. Viana, C. Vasconcelos, L. Mota-Vieira, C. Ferreira, J. Demengeot, and A. M. Vicente. 2009. Low frequency of CD4+CD25+ Treg in SLE patients: a heritable trait associated with CTLA4 and TGFbeta gene variants. BMC Immunol. 10:5.

Baumgarth. N. 2011. The double life of a B-1 cell: self-reactivity selects for protective effector functions. Nat Rev Immunol. 11:34-46.

Baumgarth, N., O. C. Herman, G. C. Jager, L. E. Brown, L. A. Herzenberg, and J. Chen. 2000. B-1 and B-2 cell-derived immunoglobulin M antibodies are nonredundant components of the protective response to influenza virus infection. *J Exp Med.* 192:271-80.

Berland, R., and H. H. Wortis. 2002. Origins and functions of B-1 cells with notes on the role of CD5. *Annu Rev Immunol.* 20:253-300.

Best, O. G., R. E. Ibbotson, A. E. Parker, Z. A. Davis, J. A. Orchard, and D. G. Oscier. 2006. ZAP-70 by flow cytometry: a comparison of different antibodies, anticoagulants, and methods of analysis. *Cytometry B Clin Cytom.* 70:235-41.

Bijl, M., G. Horst, P. C. Limburg, and C. G. Kallenberg. 2001. Expression of costimulatory molecules on peripheral blood lymphocytes of patients with systemic lupus erythematosus. Ann Rheum Dis. 60:523-6.

Binder, C. J., and G. J. Silverman. 2005. Natural antibodies and the autoimmunity of atherosclerosis. *Springer Semin Immunopathol.* 26:385-404.

Boes, M., A. P. Prodeus, T. Schmidt, M. C. Carroll, and J. Chen. 1998. A critical role of natural immunoglobulin M in immediate defense against systemic bacterial infection. *J Exp Med.* 188:2381-6.

Briles, D. E., M. Nahm, K. Schroer, J. Davie, P. Baker, J. Kearney, and R. Barletta. 1981. Antiphosphocholine antibodies found in normal mouse serum are protective against intravenous infection with type 3 *streptococcus pneumoniae*. *J Exp Med.* 153:694-705.

Burastero, S. E., P. Casali, R. L. Wilder, and A. L. Notkins. 1988. Monoreactive high affinity and polyreactive low affinity rheumatoid factors are produced by CD5+ B cells from patients with rheumatoid arthritis. *J Exp Med.* 168:1979-92.

Colovai, A. I., L. Tsao, S. Wang, H. Lin, C. Wang, T. Seki, J. G. Fisher, M. Menes, G. Bhagat, B. Alobeid, and N. Suciu-Foca. 2007. Expression of inhibitory receptor ILT3 on neoplastic B cells is associated with lymphoid tissue involvement in chronic lymphocytic leukemia. *Cytometry B Clin Cytom.* 72:354-62.

Cong, Y. Z., E. Rabin, and H. H. Wortis. 1991. Treatment of murine CD5-B cells with anti-Ig, but not LPS, induces surface CD5: two B-cell activation pathways. *Int Immunol.* 3:467-76.

Damle, R. N., T. Wasil, F. Fais, F. Ghiotto, A. Valetto, S. L. Allen, A. Buchbinder, D. Budman, K. Dittmar, J. Kolitz, S. M. Lichtman, P. Schulman, V. P. Vinciguerra, K. R. Rai, M. Ferrarini, and N. Chiorazzi. 1999. Ig V gene mutation status and CD38 expression as novel prognostic indicators in chronic lymphocytic leukemia. *Blood.* 94:1840-7.

Dauphinee, M., Z. Tovar, and N. Talal. 1988. B cells expressing CD5 are increased in Sjogren's syndrome. *Arthritis Rheum.* 31:642-7.

Dorshkind, K., and E. Montecino-Rodriguez. 2007. Fetal B-cell lymphopoiesis and the emergence of B-1-cell potential. *Nat Rev Immunol.* 7:213-9.

Duan, B., and L. Morel. 2006. Role of B-1a cells in autoimmunity. Autoimmun Rev. 5:403-8.

Ehrhardt, G. R., J. T. Hsu, L. Gartland, C. M. Leu, S. Zhang, R. S. Davis, and M. D. Cooper. 2005. Expression of the immunoregulatory molecule FcRH4 defines a distinctive tissue-based population of memory B cells. J Exp Med. 202:783-91.

Eming, R., A. Nagel, S. Wolff-Franke, E. Podstawa, D. Debus, and M. Hertl. 2008. Rituximab exerts a dual effect in pemphigus vulgaris. J Invest Dermatol. 128:2850-8.

Forster, I., and K. Rajewsky. 1987. Expansion and functional activity of Ly-1+ B cells upon transfer of peritoneal cells into allotype-congenic, newborn mice. *Eur J Immunol.* 17:521-8.

Forster, I., H. Gu, and K. Rajewsky. 1988. Germline antibody V regions as determinants of clonal persistence and malignant growth in the B cell compartment. *Embo J.* 7:3693-703.

Freedman, A. S., G. Freeman, J. Whitman, J. Segil, J. Daley, and L. M. Nadler. 1989. Studies of in vitro activated CD5+ B cells. *Blood* 73:202-8.

Ghosn, E. E., Y. Yang, J. Tung, and L. A. Herzenberg. 2008. CD11b expression distinguishes sequential stages of peritoneal B-1 development. Proc Natl Acad Sci USA. 105:5195-200.

Good, K. L., D. T. Avery, and S. G. Tangye. 2009. Resting human memory B cells are intrinsically programmed for enhanced survival and responsiveness to diverse stimuli compared to naive B cells. *J Immunol.* 182:890-901.

Griffin, D. O., N. E. Holodick, and T. L. Rothstein. 2011. Human B1 cells in umbilical cord and adult peripheral blood express the novel phenotype CD20+CD27+CD43+ CD70. J Exp Med. 208:67-80.

Gu, H., I. Forster, and K. Rajewsky. 1990. Sequence homologies, N sequence insertion and JH gene utilization in VHDJH joining: implications for the joining mechanism and the ontogenetic timing of Lyl B cell and B-CLL progenitor generation. *Embo J.* 9:2133-40.

Haas, K. M., J. C. Poe, D. A. Steeber, and T. F. Tedder. 2005. B-1a and B-1b cells exhibit distinct developmental requirements and have unique functional roles in innate and adaptive immunity to *S. pneumoniae. Immunity.* 23:7-18.

Hambleton, S., S. Salem, J. Bustamante, V. Bigley, S. Boisson-Dupuis, J. Azevedo, A. Fortin, M. Haniffa, L. Ceron-Gutierrez, C. M. Bacon, G. Menon, C. Trouillet, D. McDonald, P. Carey, F. Ginhoux, L. Alsina, T. J. Zumwalt, X. F. Kong, D. Kumararatne, K. Butler, M. Hubeau, J. Feinberg, S. Al-Muhsen, A. Cant, L. Abel, D. Chaussabel, R. Doffinger, E. Talesnik, A. Grumach, A. Duarte, K. Abarca, D. Moraes-Vasconcelos, D. Burk, A. Berghuis, F. Geissmann, M. Collin, J. L. Casanova, and P. Gros. 2011. IRF8 Mutations and Human Dendritic-Cell Immunodeficiency. N Engl J Med. 365:127-138.

Hamblin, T. J., Z. Davis, A. Gardiner, D. G. Oscier, and F. K. Stevenson. 1999. Unmutated Ig V(H) genes are associated with a more aggressive form of chronic lymphocytic leukemia. *Blood.* 94:1848-54.

Hardy, R. R., and K. Hayakawa. 2001. B cell development pathways. Annu Rev *Immunol.* 19:595-621.

Hardy, R. R., C. E. Carmack, S. A. Shinton, R. J. Riblet, and K. Hayakawa. 1989. A single VH gene is utilized predominantly in anti-BrMRBC hybridomas derived from purified Ly-1 B cells. Definition of the VH11 family. *J Immunol.* 142:3643-51.

Hastings, W. D., J. R. Tumang, T. W. Behrens, and T. L. Rothstein. 2006. Peritoneal B-2 cells comprise a distinct B-2 cell population with B-1b-like characteristics. *Eur J Immunol.* 36:1114-23.

Hayakawa, K., R. R. Hardy, A. M. Stall, and L. A. Herzenberg. 1986. Immunoglobulin-bearing B cells reconstitute and maintain the murine Ly-1 B cell lineage. Eur J Immunol. 16:1313-6.

Herzenberg, L. A. 2000. B-1 cells: the lineage question revisited. *Immunol Rev.* 175:9-22.

Herzenberg, L. A., and J. W. Tung. 2006. B cell lineages: documented at last! Nat Immunol. 7:225-6.

Holodick, N. E., J. R. Tumang, and T. L. Rothstein. 2009b. Continual signaling is responsible for constitutive ERK phosphorylation in B-1a cells. *Mol Immunol.* 46:3029

Holodick, N. E., J. R. Tumang, and T. L. Rothstein. 2010. B1 cells constitutively secrete IgM independently of IRF4. Eur J Immunol. 40:3007-16.

Holodick, N. E., K. Repetny, X. Zhong, and T. L. Rothstein. 2009a. Adult BM generates CD5+ B1 cells containing abundant N-region additions. *Eur J Immunol.* 39:2383-94.

Ishida, H., R. Hastings, J. Kearney, and M. Howard. 1992. Continuous anti-interleukin 10 antibody administration depletes mice of Ly-1 B cells but not conventional B cells. *J Exp Med.* 175:1213-20.

Jacob, N., and W. Stohl. 2010. Autoantibody-dependent and autoantibody-independent roles for B cells in systemic lupus erythematosus: past, present, and future. Autoimmunity. 43:84-97.

Jacobi, A. M., K. Reiter, M. Mackay, C. Aranow, F. Hiepe, A. Radbruch, A. Hansen, G. R. Burmester, B. Diamond, P. E. Lipsky, and T. Dorner. 2008. Activated memory B cell subsets correlate with disease activity in systemic lupus erythematosus: delineation by expression of CD27, IgD, and CD95. Arthritis Rheum. 58:1762-73.

Jego, G., R. Bataille, and C. Pellat-Deceunynck. 2001. Interleukin-6 is a growth factor for nonmalignant human plasmablasts. *Blood.* 97:1817-22.

Jung, G., J. C. Eisenmann, S. Thiebault, and P. Henon. 2003. Cell surface CD43 determination improves diagnostic precision in late B-cell diseases. *Br J Haematol.* 120:496-9.

Kantor, A. B., A. M. Stall, S. Adams, K. Watanabe, and L. A. Herzenberg. 1995. De novo development and self-replenishment of B cells. *Int Immunol.* 7:55-68.

Kantor, A. B., and L. A. Herzenberg. 1993. Origin of murine B cell lineages. *Annu Rev Immunol.* 11:501-38.

Karras, J. G., Z. Wang, L. Huo, R. G. Howard, D. A. Frank, and T. L. Rothstein. 1997. Signal transducer and activator of transcription-3 (STAT3) is constitutively activated in normal, self-renewing B-1 cells but only inducibly expressed in conventional B lymphocytes. *J Exp Med.* 185:1035-42.

Kassianos, A. J., S. L. Jongbloed, D. N. Hart, and K. J. Radford. 2010. Isolation of human blood DC subtypes. Methods Mol Biol. 595:45-54.

Klein, U., and R. Dalla-Favera. 2007. Unexpected steps in plasma-cell differentiation. *Immunity.* 26:543-4.

Klein, U., K. Rajewsky, and R. Kuppers. 1998. Human immunoglobulin (Ig)M+IgD+ peripheral blood B cells expressing the CD27 cell surface antigen carry somatically mutated variable region genes: CD27 as a general marker for somatically mutated (memory) B cells. *J Exp Med.* 188:1679-89.

Kroese, F. G., W. A. Ammerlaan, and A. B. Kantor. 1993. Evidence that intestinal IgA plasma cells in mu, kappa transgenic mice are derived from B-1 (Ly-1 B) cells. *Int Immunol.* 5:1317-27.

Kruetzmann, S., M. M. Rosado, H. Weber, U. Germing, O. Tountilhae, H. H. Peter, R. Berner, A. Peters, T. Boehm, A. Plebani, I. Quinti, and R. Carsetti. 2003. Human immunoglobulin M memory B cells controlling Streptococcus pneumoniae infections are generated in the spleen. *J Exp Med.* 197:939-45.

Lee, J., S. Kuehen, R. Fischer, S. Chang, and P. E. Lipsky. 2009. Identification and characterization of a human CD5+ pre-naive B cell population. *J Immunol.* 182:4116-26.

Liossis, S. N., and P. P. Sfikakis. 2008. Rituximab-induced B cell depletion in autoimmune diseases: potential effects on T cells. Clin Immunol. 127:280-5.

Lund, F. E., and T. D. Randall. 2010. Effector and regulatory B cells: modulators of CD4(+) T cell immunity. Nat Rev Immunol. 10:236-47.

Maurer, D., W. Holter, 0. Majdic, G. F. Fischer, and W. Knapp. 1990. CD27 expression by a distinct subpopulation of human B lymphocytes. *Eur J Immunol.* 20:2679-84.

Mohan, C., L. Morel, P. Yang, and E. K. Wakeland. 1998. Accumulation of splenic B1a cells with potent antigen-presenting capability in NZM2410 lupus-prone mice. Arthritis Rheum. 41:1652-62.

Montecino-Rodriguez, E., H. Leathers, and K. Dorshkind. 2006. Identification of a B-1 B cell-specified progenitor. *Nat Immunol.* 7:293-301.

Morris, D. L., and T. L. Rothstein. 1994. CD5+ B (B-1) cells and immunity. In Handbook of B and T Lymphocytes. E. C. Snow, editor. Academic Press, Inc., San Diego. 421-45.

Nilsson, A., A. de Milito, F. Mowafi, G. Winberg, O. Bjork, E. Z. Wolpert, and F. Chiodi. 2005. Expression of CD27–CD70 on early B cell progenitors in the bone marrow: implication for diagnosis and therapy of childhood ALL. *Exp Hematol.* 33:1500-7.

Ochsenbein, A. F., T. Fehr, C. Lutz, M. Suter, F. Brombacher, H. Hengartner, and R. M. Zinkemagel. 1999. Control of early viral and bacterial distribution and disease by natural antibodies. *Science.* 286:2156-9.

Pennell, C. A., T. J. Mercolino, T. A. Grdina, L. W. Arnold, G. Haughton, and S. H. Clarke. 1989. Biased immunoglobulin variable region gene expression by Ly-1 B cells due to clonal selection. *Eur J Immunol.* 19:1289-95.

Perosa, F., M. Prete, V. Racanelli, and F. Dammacco. 2010. CD20-depleting therapy in autoimmune diseases: from basic research to the clinic. J Intern Med. 267:260-77.

Plater-Zyberk, C., R. N. Maini, K. Lam, T. D. Kennedy, and G. Janossy. 1985. A rheumatoid arthritis B cell subset expresses a phenotype similar to that in chronic lymphocytic leukemia. *Arthritis Rheum.* 28:971-6.

Rakhmanov, M., B. Keller, S. Gutenberger, C. Foerster, M. Hoenig, G. Driessen, M. van der Burg, J. J. van Dongen, E. Wiech, M. Visentini, I. Quinti, A. Prasse, N. Voelxen, U. Salzer, S. Goldacker, P. Fisch, H. Eibel, K. Schwarz, H. H. Peter, and K. Warnatz. 2009. Circulating CD21low B cells in common variable immunodeficiency resemble tissue homing, innate-like B cells. Proc Natl Acad Sci USA. 106:13451-6.

Raman, C., and K. L. Knight. 1992. CD5+ B cells predominate in peripheral tissues of rabbit. *J Immunol.* 149:3858-64.

Reininger, L., T. H. Winkler, C. P. Kalberer, M. Jourdan, F. Melchers, and A. G. Rolink. 1996. Intrinsic B cell defects in NZB and NZW mice contribute to systemic lupus erythematosus in (NZB×NZW) F1 mice. J Exp Med. 184: 853-61.

Rothstein, T. L. 2002. Cutting edge commentary: two B-1 or not to be one. *J Immunol.* 168:4257-61.

Sanz, I., and F. E. Lee. 2010. B cells as therapeutic targets in SLE. Nat Rev Rheumatol. 6:326-37.

Shi, Y., T. Yamazaki, Y. Okubo, Y. Uehara, K. Sugane, and K. Agematsu. 2005. Regulation of aged humoral immune defense against pneumococcal bacteria by IgM memory B cell. *J Immunol.* 175:3262-7.

Sidman, C. L., L. D. Shultz, R. R. Hardy, K. Hayakawa, and L. A. Herzenberg. 1986. Production of immunoglobulin isotypes by Ly-1+ B cells in viable motheaten and normal mice. *Science.* 232:1423-5.

Sims, G. P., R. Ettinger, Y. Shirota, C. H. Yarboro, G. G. Illei, and P. E. Lipsky. 2005. Identification and characterization of circulating human transitional B cells. *Blood.* 105:4390-8.

Stasi, R., G. Del Poeta, E. Stipa, M. L. Evangelista, M. M. Trawinska, N. Cooper, and S. Amadori. 2007. Response to B-cell depleting therapy with rituximab reverts the abnormalities of T-cell subsets in patients with idiopathic thrombocytopenic purpura. Blood. 110:2924-30.

Taniguchi, O., H. Miyajima, T. Hirano, M. Noguchi, A. Ueda, H. Hashimoto, S. Hirose, and K. Okumura. 1987. The Leu-1 B-cell subpopulation in patients with rheumatoid arthritis. *J Clin Immunol.* 7:441-8.

Tumang, J. R., R. Frances, S. G. Yeo, and T. L. Rothstein. 2005. Cutting edge: Spontaneously Ig-secreting B-1 cells violate the accepted paradigm for expression of differentiation-associated transcription factors. JImmunol. 174:3173-7.

Wang, X., and B. D. Stollar. 2000. Human immunoglobulin variable region gene analysis by single cell RT-PCR. *J Immunol Methods.* 244:217-25.

Wardemann, H., T. Boehm, N. Dear, and R. Carsetti. 2002. B-1a B cells that link the innate and adaptive immune responses are lacking in the absence of the spleen. *J Exp Med.* 195:771-80.

Weller, S., M. C. Braun, B. K. Tan, A. Rosenwald, C. Cordier, M. E. Conley, A. Plebani, D. S. Kumararatne, D. Bonnet, O. Toumilhac, G. Tchernia, B. Steiniger, L. M. Staudt, J. L. Casanova, C. A. Reynaud, and J. C. Weill. 2004. Human blood IgM "memory" B cells are circulating splenic marginal zone B cells harboring a prediversified immunoglobulin repertoire. Blood. 104:3647-54.

Wells, S. M., A. B. Kantor, and A. M. Stall. 1994. CD43 (S7) expression identifies peripheral B cell subsets. JImmunol. 153:5503-15.

Wilson, S. M., and B. N. Wilkie. 2007. B-1 and B-2 B-cells in the pig cannot be differentiated by expression of CD5. *Vet Immunol Immunopathol.* 115:10-6.

Wong, S. C., W. K. Chew, J. E. Tan, A. J. Melendez, F. Francis, and K. P. Lam. 2002. Peritoneal CD5+ B-1 cells have signaling properties similar to tolerant B cells. *J Biol Chem.* 277:30707-15.

Xu, Z., E. J. Butfiloski, E. S. Sobel, and L. Morel. 2004. Mechanisms of peritoneal B-1a cells accumulation induced by murine lupus susceptibility locus Sle2. J Immunol. 173:6050-8.

Zhong, X., W. Gao, N. Degauque, C. Bai, Y. Lu, J. Kenny, M. Oukka, T. B. Strom, and T. L. Rothstein. 2007. Reciprocal generation of Th1/Th17 and T(reg) cells by B1 and B2 B cells. *Eur J Immunol.* 37:2400-4.

Zouali, M. 2008. B lymphocytes—chief players and therapeutic targets in autoimmune diseases. Front Biosci. 13:4852-61.

What is claimed is:

1. A method of isolating a population of human natural immunoglobulin-producing B1 lymphocytes from a human blood sample, wherein the B1 lymphocytes co-express surface biomarkers CD20 and CD43 and CD27, comprising isolating B lymphocytes from the sample that co-express surface biomarkers CD20 and CD43 and CD27 by contacting the sample with fluorescently labelled antibodies directed to CD20 and CD43 and CD27 and obtaining the fluorescently labelled B1 lymphocytes by fluorescence-activated cell sorting (FACS).

2. The method of claim 1, wherein the sample is umbilical cord blood or peripheral blood.

3. The method of claim 1, wherein the B1 lymphocytes co-express surface biomarker CD11b.

4. The method of claim 1, wherein the B1 lymphocytes do not co-express surface biomarker CD11b.

5. The method of claim 1, further comprising obtaining mononuclear cells in the sample via density gradient separation prior to contacting with labelled antibodies.

6. The method of claim 1, further comprising culturing isolated B1 lymphocytes co-expressing surface biomarkers CD20 and CD43 and CD27 obtained by the method.

* * * * *